(12) United States Patent
Komyoji et al.

(10) Patent No.: US 8,119,569 B2
(45) Date of Patent: Feb. 21, 2012

(54) BENZOYLPYRAZOLE COMPOUNDS, PROCESS FOR THEIR PRODUCTION AND HERBICIDES CONTAINING THEM

(75) Inventors: Terumasa Komyoji, Gamo-gun (JP); Masamitsu Tsukamoto, Kusatsu (JP); Hiroshi Kikugawa, Kusatsu (JP); Hiroshi Hata, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 224 days.

(21) Appl. No.: 12/513,512

(22) PCT Filed: Nov. 9, 2007

(86) PCT No.: PCT/JP2007/072239
§ 371 (c)(1),
(2), (4) Date: May 5, 2009

(87) PCT Pub. No.: WO2008/065907
PCT Pub. Date: Jun. 5, 2008

(65) Prior Publication Data
US 2010/0075855 A1   Mar. 25, 2010

(30) Foreign Application Priority Data

Nov. 28, 2006 (JP) .................................. 2006-319579

(51) Int. Cl.
*A01N 43/56* (2006.01)
*C07D 231/10* (2006.01)
(52) U.S. Cl. .................................... 504/282; 548/369.4
(58) Field of Classification Search ......................... None
See application file for complete search history.

(56) References Cited

U.S. PATENT DOCUMENTS 4,948,887 A   8/1990   Baba et al.
4,986,845 A   1/1991   Oya et al.

FOREIGN PATENT DOCUMENTS

EP   0 282 944   9/1988
EP   0 352 543   1/1990

OTHER PUBLICATIONS

U.S. Appl. No. 12/993,760, filed Nov. 19, 2010, Tsukamoto, et al.
U.S. Appl. No. 13/133,993, filed Jun. 10, 2011, Kikugawa, et al.

*Primary Examiner* — Kamal Saeed
(74) *Attorney, Agent, or Firm* — Oblon, Spivak, McClelland, Maier & Neustadt, L.L.P.

(57) ABSTRACT

The present invention provides a novel herbicide showing excellent herbicidal effects, which has a wide application range including agricultural fields and non-agricultural fields and various application methods including soil treatment and foliage treatment. A benzoylpyrazole compound represented by the formula (I) or its salt: wherein $R_1$ is alkyl, $R_2$ is a hydrogen atom or alkyl, $R_3$ is alkyl, $R_4$ is alkyl or halogen, $R_5$ is alkyl substituted by one $Y_1$, haloalkoxy, alkoxy substituted by one $Y_2$, or alkoxycarbonyl, $R_6$ is alkylsulfonyl, A is alkylene substituted by at least one alkyl, $Y_1$ is alkoxy or haloalkoxy, and $Y_2$ is alkoxy; a process for its production; a herbicide containing it as an active ingredient; and a method for controlling undesired plants or inhibiting their growth, which comprises applying a herbicidally effective amount thereof to the undesired plants or to a place where they grow.

10 Claims, No Drawings

BENZOYLPYRAZOLE COMPOUNDS, PROCESS FOR THEIR PRODUCTION AND HERBICIDES CONTAINING THEM

TECHNICAL FIELD

The present invention relates to novel benzoylpyrazole compounds useful as an active ingredient of herbicides.

BACKGROUND ART

EP0352543A and EP0282944A disclose benzoylpyrazole compounds. However, benzoylpyrazole compounds represented by the following formula (I) are not specifically disclosed therein.

DISCLOSURE OF THE INVENTION

Object to be Accomplished by the Invention

Heretofore, herbicides which have excellent herbicidal activities against weeds and which are safe to crop plants, have been desired for labor saving in the operation of controlling weeds and for improvement of productivity of agricultural and horticultural plants. In development of new herbicides in future, it is desired to develop compounds capable of exhibiting desired herbicidal activities while their dosages are controlled to be low. Further, it is desired to develop compounds which will not remain in soil more than necessary while exhibiting practical residual effectiveness. Further, it is desired to develop compounds which are highly safe to animals. However, search for novel compounds suitable for such an object depends on trial and error.

Means to Accomplish the Object

The present inventors have conducted extensive studies on benzoylpyrazole compounds in order to find more excellent herbicides which accomplish the above object and as a result, accomplished the present invention.

Namely, the present invention relates to a benzoylpyrazole compound represented by the formula (I) or its salt:

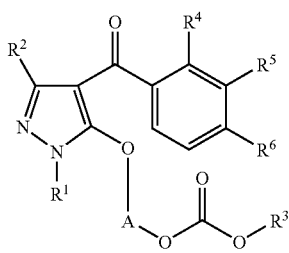

(I)

wherein $R^1$ is alkyl, $R^2$ is a hydrogen atom or alkyl, $R^3$ is alkyl, $R^4$ is alkyl or halogen, $R^5$ is alkyl substituted by one $Y^1$, haloalkoxy, alkoxy substituted by one $Y^2$, or alkoxycarbonyl, $R^6$ is alkylsulfonyl, A is alkylene substituted by at least one alkyl, $Y^1$ is alkoxy or haloalkoxy, and $Y^2$ is alkoxy; a process for producing it; a herbicide containing it as an active ingredient; and a method for controlling undesired plants or inhibiting their growth, which comprises applying a herbicidally effective amount of it to the undesired plants or to a place where they grow.

The compounds represented by the formula (I) realize a remarkable improvement in the herbicidal activities against weeds as compared with conventional compounds of similar types and have a high safety to crop plants.

BEST MODE FOR CARRYING OUT THE INVENTION

In the above formula (I), the alkyl or alkyl moiety may be linear or branched, and specific examples thereof include $C_{1-9}$ alkyl such as methyl, ethyl, n-propyl, iso-propyl, n-butyl, iso-butyl, sec-butyl, tert-butyl, n-pentyl, iso-pentyl, neopentyl, tert-pentyl, n-hexyl, iso-hexyl, n-heptyl, n-octyl and n-nonyl.

In the above formula (I), the halogen or halogen as a substituent may be an atom of fluorine, chlorine, bromine or iodine. The number of halogens as substituents may be one or more, and if more, they may be the same or different. Further, the positions for substitution of such halogens may be any positions.

In the above formula (I), the alkylene moiety may be a $C_{1-9}$ alkylene such as methylene, ethylene, trimethylene, tetramethylene, pentamethylene, hexamethylene, heptamethylene, octamethylene or nonamethylene.

The salt of the benzoylpyrazole compound represented by the above formula (I) includes all kinds of salts so long as they are agriculturally acceptable. Examples thereof include alkali metal salts such as a sodium salt and a potassium salt; alkaline earth metal salts such as a magnesium salt and a calcium salt; amine salts such as a dimethylamine salt and a triethylamine salt; inorganic acid salts such as a hydrochloride, a perchlorate, a sulfate and a nitrate; and organic acid salts such as an acetate and a methanesulfonate.

For the benzoylpyrazole compounds represented by the above formula (I), optical isomers may sometimes be present, and the present invention includes all of such isomers. In this specification, the compound is described as a mixture of isomers, unless otherwise specified.

The benzoylpyrazole compound represented by the above formula (I) or its salt (hereinafter referred to simply as the compound of the present invention) can be produced by the following reaction (A) and in accordance with a usual method for producing a salt.

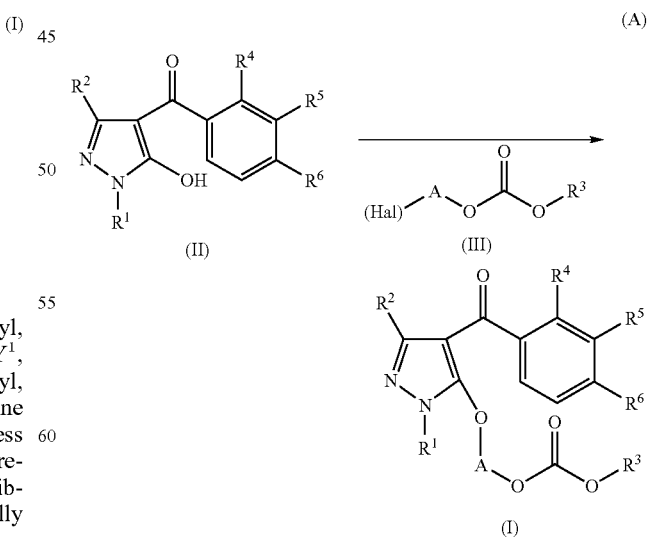

(A)

wherein $R^1$, $R^2$, $R^3$, $R^4$, $R^5$, $R^6$ and A are as defined above, and Hal is halogen.

The above reaction can be carried out in the presence of a solvent, as the case requires. The solvent may be any solvent so long as it is inert to the reaction. It may, for example, be a ketone such as acetone, ethyl methyl ketone or diethyl ketone; a halogenated hydrocarbon such as methylene chloride, chloroform, dichloroethane or trichloroethane; an aromatic hydrocarbon such as benzene, toluene, xylene, or nitrobenzene; an ester such as methyl acetate, ethyl acetate or propyl acetate; an aprotic polar solvent such as acetonitrile, N,N-dimethylformamide (DMF), dimethylsulfoxide (DMSO), dimethylacetamide (DMA), hexamethyl phosphoric acid triamide (HMPA) or sulfolane; or an ether such as diethyl ether, dioxane, tetrahydrofuran (THF) or dimethoxyethane. As the solvent, one or more of them may suitably be selected.

The above reaction can be carried out in the presence of a base, as the case requires. The base may be either an inorganic base or an organic base. The organic base may, for example be a tertiary amine such as triethylamine or diisopropylethylamine; pyridine, 4-(dimethylamino)pyridine, or 2,6-lutidine. The inorganic base may, for example, be an alkali metal carbonate such as sodium carbonate or potassium carbonate; an alkali metal hydrogencarbonate such as sodium hydrogencarbonate or potassium hydrogencarbonate; an alkaline earth metal carbonate such as calcium carbonate or barium carbonate; an alkali metal hydroxide such as sodium hydroxide or potassium hydroxide; or an alkali metal cyanide such as sodium cyanide or potassium cyanide. With respect to such bases, one or more of them may suitably be selected and mixed for use, in an amount of from 0.01 to 100 equivalents to the compound of the formula (II).

The above reaction may be carried out in the presence of a catalyst. The catalyst may, for example, be n-butyl ammonium bromide, n-butyl ammonium chloride, tetra-n-butylphosphonium bromide, sodium iodide or potassium iodide.

The above reaction can be carried out at a reaction temperature of usually from 0° C. to 150° C. for a reaction time of usually from 1 minute to 48 hours.

The compound represented by the above formula (II) may be produced in accordance with the following reaction (B).

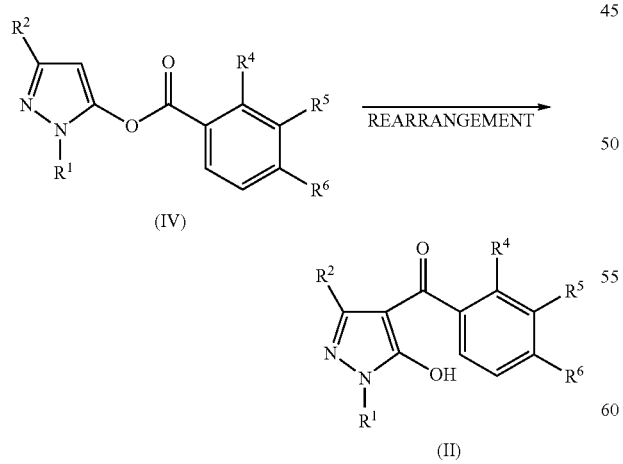

(B)

wherein $R^1$, $R^2$, $R^4$, $R^5$ and $R^6$ are as defined above.

Namely, the compound represented by the formula (II) can be produced by subjecting a compound represented by the formula (IV) to a rearrangement reaction.

The above reaction can be carried out in the presence of a solvent, as the case requires. The solvent may be any solvent so long as it is inert to the reaction. It may, for example, be a halogenated hydrocarbon such as methylene chloride, chloroform, dichloroethane or trichloroethane; an aromatic hydrocarbon such as benzene, toluene, xylene or nitrobenzene; an ester such as methyl acetate, ethyl acetate or propyl acetate; an aprotic polar solvent such as acetonitrile, DMF, DMSO, DMA, HMPA or sulfolane; or an ether such as diethyl ether, dioxane, THF or dimethoxyethane. As the solvent, one or more of them may suitably be selected.

The above reaction can be carried out in the presence of a base, as the case requires. The base may be either an organic base or an inorganic base, and those exemplified in the above reaction (A) may, for example, be mentioned. With respect to these bases, one or more of them may suitably be selected and mixed for use in an amount of from 0.01 to 100 equivalents to the compound of the formula (IV).

Further, in the above reaction, a catalyst may be added as the case requires. As such a catalyst, acetone cyanohydrin may be used from 0.01 to 10 equivalents to the compound of the formula (IV).

The above reaction can be carried out at a reaction to temperature of usually from 0° C. to 150° C. for a reaction time of usually from 1 minute to 48 hours.

The compound represented by the above formula (IV) may be prepared in accordance with the following reaction (C).

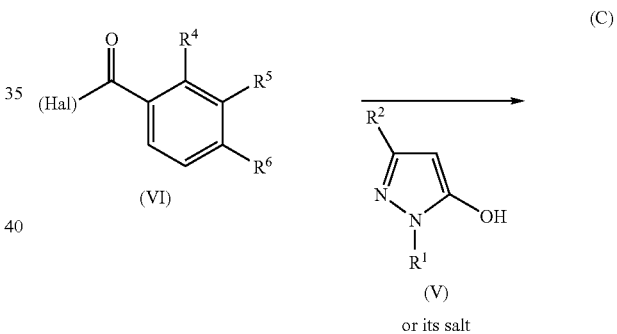

(C)

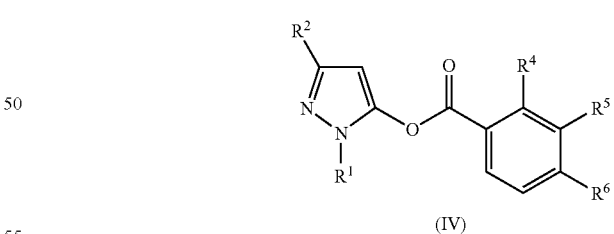

(IV)

wherein $R^1$, $R^2$, $R^4$, $R^5$, $R^6$ and Hal are as defined above.

Namely, the compound represented by the formula (IV) can be produced by reacting a compound represented by the formula (V) or its salt, such as a hydrochloride, a sulfate or a nitrate, with a compound represented by the formula (VI).

The above reaction can be carried out in the presence of a solvent, as the case requires. The solvent may be any solvent so long as it is inert to the reaction, and those exemplified in the above reaction (B) may, for example, be mentioned. One or more of them may suitably be selected.

The above reaction can be carried out in the presence of a base, as the case requires. The base may be an organic base or an inorganic base, and those exemplified in the above reaction (A) may, for example, be mentioned. With respect to such these bases, one or more of them may suitably be selected and mixed for use in an amount of from 1 to 100 equivalents to the compound of the formula (VI).

The reaction temperature for the above reaction is usually from 0° C. to 150° C., and the reaction time is usually from 1 minute to 48 hours.

The compound represented by the above formula (VI) can be produced in accordance with the following reaction (D).

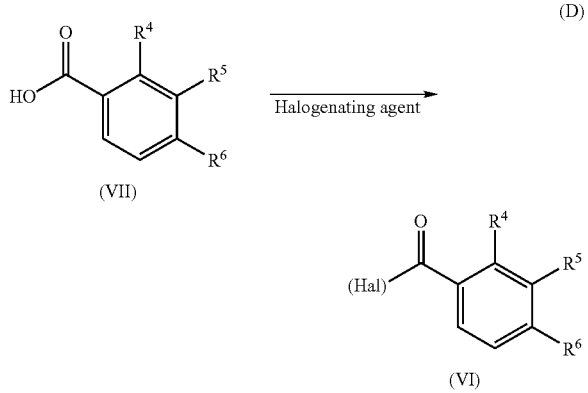

wherein $R^4$, $R^5$, $R^6$ and Hal are as defined above.

In the above reaction, a halogenating agent such as thionyl chloride or oxalyl chloride is reacted in an amount of from 1 to 100 equivalents to the compound represented by the formula (VII).

The above reaction can be carried out in the presence of a solvent, as the case requires. The solvent may be any solvent so long as it is a solvent inert to the reaction, and those exemplified in the above reaction (B) may, for example, be mentioned. One or more of them may suitably be selected.

For the above reaction, a catalyst may be used as the case requires. The catalyst may, for example, be DMF.

The reaction temperature for the above reaction is usually from 0° C. to 150° C., and the reaction time is usually from 1 minute to 48 hours.

The compound represented by the above formula (IV) can be produced in accordance with the following reaction (E), other than the above-mentioned methods.

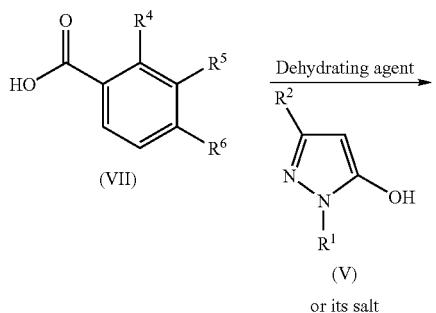

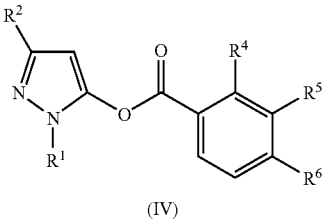

wherein $R^1$, $R^2$, $R^4$, $R^5$ and $R^6$ are as defined above.

Namely, the compound represented by the formula (IV) can be produced by reacting a compound represented by the formula (V) or its salt, such as a hydrochloride, a sulfate or a nitrate, with a compound represented by the formula (VII) by means of a dehydrating agent.

The dehydrating agent to be used for the above reaction may, for example, be DCC (dicyclohexylcarbodiimide) or 1-ethyl-3-(3-(dimethylaminopropyl)-carbodiimide hydrochloride.

The above reaction can be carried out in the presence of a solvent, as the case requires. The solvent may be any solvent so long as it is inert to the reaction, and those exemplified in the above reaction (B) may, for example, be mentioned. One or more of them may suitably be selected.

The above reaction can be carried out in the presence of a base, as the case requires. The base may, for example, be a tertiary amine such as triethylamine and diisopropylethylamine; pyridine, 4-(dimethylamino)pyridine or 2,6-lutidine. As the base, one or more of them may suitably be selected and mixed for use in an amount of from 1 to 100 equivalents to the compound represented by the formula (VII).

The above reaction can be carried out at a reaction temperature of usually from 0° C. to 150° C. for a reaction time of usually from 1 minute to 48 hours.

The compound represented by the above formula (VII) can be produced in accordance with the following reaction (F).

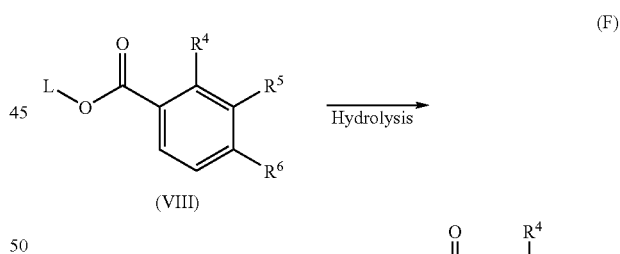

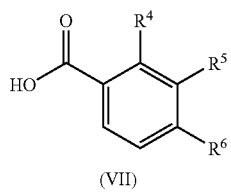

wherein $R^4$, $R^5$ and $R^6$ are as defined above, and L is a protective group such as alkyl.

The compound represented by the formula (VII) can be produced by subjecting a compound represented by the formula (VIII) to hydrolysis in the presence of water.

The above reaction can be carried out in the presence of a solvent, as the case requires. The solvent may be any solvent so long as it is inert to the reaction, and it may, for example, be an aromatic hydrocarbon such as benzene, toluene or xylene; an aprotic polar solvent such as acetonitrile, DMF, DMSO, DMA, HMPA or sulfolane; an ether such as diethyl ether, dioxane, THF or dimethoxyethane; an alcohol such as methanol or ethanol; or water. As the solvent, one or more of them may suitably be selected.

The above reaction can be carried out in the presence of a base or an acid, as the case requires. The base may be either an organic base or an inorganic base, and those exemplified in the above reaction (A) may, for example, be mentioned. The acid may, for example, be hydrochloric acid, sulfuric acid or perchloric acid. As the base or acid, one or more of them may suitably be selected and mixed for use in an amount of from 1 to 100 equivalents to the compound represented by the formula (VIII).

The above reaction can be carried out at a reaction temperature of usually from 0° C. to 150° C. for a reaction time of usually from 1 minute to 48 hours.

Among the compounds represented by the above formula (VIII), a compound wherein $R^5$ is $R^{5-a-1}$ can be produced in accordance with the following reaction (G).

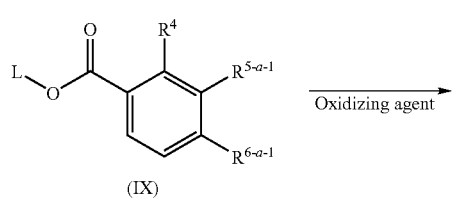

(G)

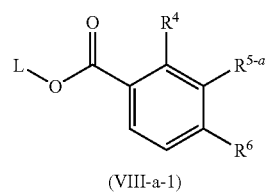

(VIII-a-1)

wherein $R^{5-a-1}$ is alkoxy substituted by one $Y^2$, or haloalkoxy, $R^{6-a-1}$ is alkylthio, and L, $R^4$, $R^6$ and $Y^2$ are as defined above.

Namely, the compound represented by the formula (VIII-a-1) can be produced by reacting a compound represented by the formula (IX) with an oxidizing agent in the presence of a solvent.

The oxidizing agent to be used in the above reaction may, for example, be hydrogen peroxide, peracetic acid or methachloroperbenzoic acid.

The solvent to be used for the above reaction may be any solvent so long as it is inert to the reaction, and it may, for example, be a halogenated hydrocarbon such as methylene chloride, chloroform, dichloroethane or trichloroethane; a ketone such as acetone or methyl ethyl ketone; an ether such as diethyl ether, dioxane, THF or dimethoxyethane; or acetic acid. As the solvent, one or more of them may suitably be selected.

The above reaction can be carried out at a reaction temperature of usually from 0° C. to 150° C. for a reaction time of usually from 1 minute to 48 hours.

The above reaction can be carried out in the presence of a catalyst, as the case requires. The catalyst may, for example, be sodium tungstate or its hydrate.

The compound represented by the above formula (IX) can be produced in accordance with the following reaction (H).

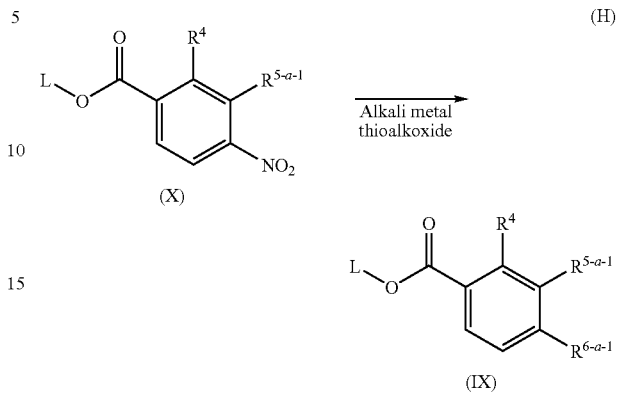

wherein L, $R^4$, $R^{5-a-1}$ and $R^{6-a-1}$ are as defined above.

Namely, the compound represented by the formula (IX) can be produced by reacting a compound represented by the formula (X) with an alkali metal thioalkoxide.

The alkali metal thioalkoxide to be used for the above reaction may, for example, be sodium thiomethoxide or sodium thioethoxide.

The above reaction can be carried out in the presence of a solvent, as the case requires. The solvent may be any solvent so long as it is inert to the reaction, and it may, for example, be an aprotic polar solvent such as acetonitrile, DMF, DMSO, DMA, HMPA, sulfolane or dimethoxyethane. As the solvent, one or more of them may suitably be selected.

The above reaction can be carried out at a reaction temperature of usually from 0° C. to 150° C. for a reaction time of usually from 1 minute to 48 hours.

The compound represented by the above formula (X) can be produced in accordance with the following reaction (I).

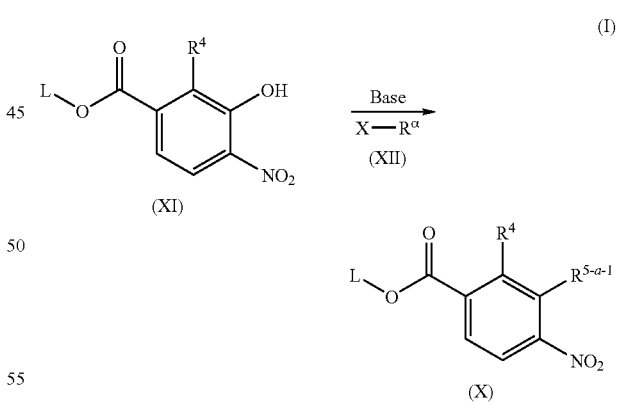

wherein $R^\alpha$ is alkyl substituted by one $Y^2$, or haloalkyl, X is a leaving group such as halogen or a methane sulfonyloxy group, and L, $R^4$, $R^{5-a-1}$ and $Y^2$ are as defined above.

Namely, the compound represented by the formula (X) can be produced by reacting a compound represented by the formula (XI) with a compound represented by the formula (XII) in the presence of a base.

The base to be used in the above reaction may be either an inorganic base or an organic base. The organic base may, for example, be triethylamine, diisopropylethylamine, pyridine, 4-(dimethylamino)pyridine or 2,6-lutidine. The inorganic base may, for example, be an alkali metal carbonate such as sodium carbonate or potassium carbonate; an alkali metal hydroxide such as sodium hydroxide or potassium hydroxide; or an alkali metal hydride such as sodium hydride or potassium hydride. As the base, one or more of them may suitably be selected and mixed for use in an amount of from 0.5 to 100 equivalents to the compound represented by the formula (XI).

The above reaction can be carried out in the presence of a solvent, as the case requires. The solvent may be any solvent so long as it is inert to the reaction, and those exemplified in the above reaction (B) may, for example be mentioned. One or more of them may suitably be selected.

The above reaction can be carried out in the presence of a catalyst, as the case requires. The catalyst may, for example, be potassium iodide or tetra-n-butylammonium iodide.

The above reaction can be carried out at a reaction temperature of usually from 0° C. to 150° C. for a reaction time of usually from 1 minute to 48 hours.

The compound represented by the above formula (VIII-a-1) can be produced in accordance with the following reaction (J), other than the above method.

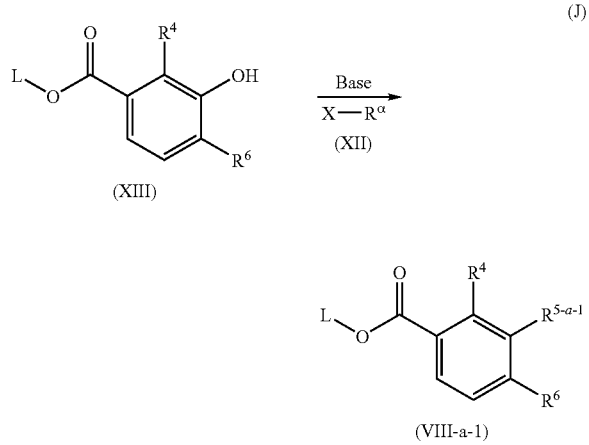

wherein L, $R^4$, $R^{5-a-1}$, $R^6$, $R^\alpha$ and X are as defined above.

Namely, the compound represented by the formula (VIII-a-1) can be produced by reacting a compound represented by the formula (XIII) with a compound represented by the formula (XII) in the presence of a base.

The above reaction can be carried out in the same manner as the above reaction (I).

The compound represented by the above formula (XIII) can be produced in accordance with the following reaction (K).

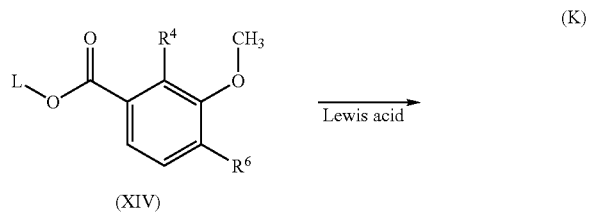

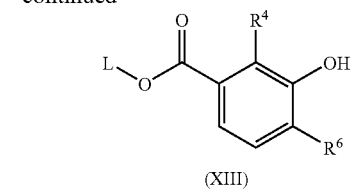

wherein $R^4$, $R^6$ and L are as defined above.

Namely, the compound represented by the formula (XIII) can be produced by reacting a compound represented by the formula (XIV) with a Lewis acid such as boron tribromide, aluminum chloride or iron bromide.

The above reaction can be carried out in the presence of a solvent, as the case requires. The solvent may be any solvent so long as it is inert to the reaction, and it may, for example, be a halogenated hydrocarbon such as methylene chloride, chloroform, dichloroethane or trichloroethane; an aromatic hydrocarbon such as benzene, toluene or xylene; or an ester such as methyl acetate, ethyl acetate or propyl acetate. As the solvent, one or more of them may be suitably selected.

The above reaction can be carried out at a reaction temperature of usually from 0° C. to 150° C. for a reaction time of usually from 1 minute to 48 hours.

The compound represented by the above formula (XIV) can be produced in accordance with the following reaction (L).

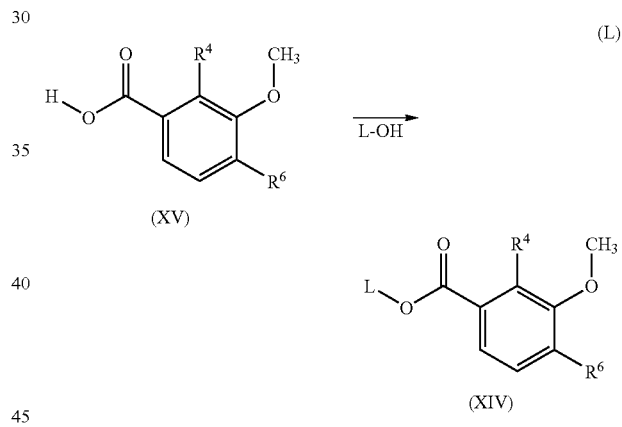

wherein $R^4$, $R^6$ and L are as defined above.

Namely, the compound represented by the formula (XIV) can be produced by a reaction of introducing a protective group L into a compound represented by the formula (XV).

The above reaction can be carried out in the presence of a solvent, as the case requires. The solvent may be any solvent so long as it is inert to the reaction, and it may, for example, be an aromatic hydrocarbon such as benzene, toluene or xylene; an ester such as methyl acetate, ethyl acetate or propyl acetate; a halogenated hydrocarbon such as methylene chloride, chloroform, dichloroethane or trichloroethane; or an aprotic polar solvent such as acetonitrile, DMF, DMSO, DMA, HMPA or sulfolane. As the solvent, one or more of them may be suitably selected.

The above reaction can be carried out in the presence of an acid, as the case requires. The acid to be used for the above reaction may, for example, be hydrochloric acid or sulfuric acid.

The above reaction can be carried out at a reaction temperature of usually from 0° C. to 150° C. for a reaction time of usually from 1 minute to 48 hours.

Among the compounds represented by the above formula (VIII), a compound wherein $R^5$ is $R^{5-a-2}$ can be produced in accordance with the following reaction (M).

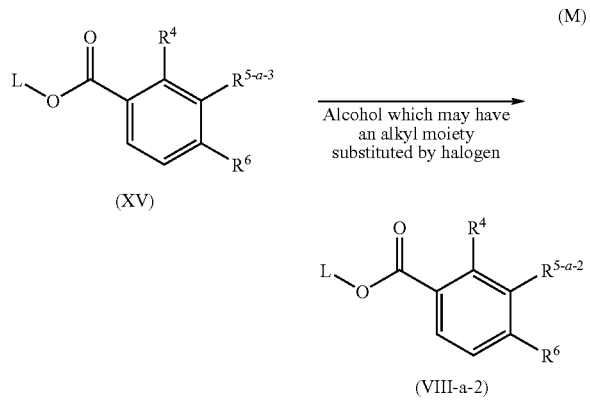

wherein $R^{5-a-2}$ is alkyl substituted by one $Y^1$, $R^{5-a-3}$ is bromoalkyl, and L, $R^4$, $R^6$ and $Y^1$ are as defined above.

The above reaction can be carried out in the presence of a solvent, as the case requires. The solvent may be any solvent so long as it is inert to the reaction, and it may, for example, be an alcohol such as methanol or ethanol; an ester such as methyl acetate, ethyl acetate or propyl acetate; an ether such as diethyl ether, dioxane, THF or dimethoxyethane; or an aprotic polar solvent such as acetonitrile, DMF, DMSO, DMA, HMPA or sulfolane. As the solvent, one or more of them may suitably be selected.

The above reaction can be carried out in the presence of a base, as the case requires. The base may, is for example, be an alkali metal hydride such as sodium hydride or potassium hydride.

The above reaction can be carried out at a reaction temperature of usually from 0° C. to 150° C. for a reaction time of usually from 1 minute to 48 hours.

The compounds of the present invention have excellent herbicidal effects when used as an active ingredient of herbicides. The application range extends to agricultural fields such as paddy fields, crop plant fields, orchards and mulberry fields and non-agricultural fields such as forest land, farm roads, play grounds and factory sites. The application method may suitably be selected from soil application, foliar application, water application, etc.

The compounds of the present invention are capable of controlling a wide range of undesired weeds, such as gramineae such as barnyardgrass (*Echinochloa crus-galli* L., *Echinochloa oryzicola* vasing.), crabgrass (*Digitaria sanguinalis* L., *Digitaria ischaemum* Muhl., *Digitaria adscendens* Henr., *Digitaria microbachne* Henr., *Digitaria horizontalis* Willd.), green foxtail (*Setaria viridis* L.), giant foxtail (*Setaria faberi* Herrm.), yellow foxtail (*Setaria lutescens* Hubb.), goosegrass (*Eleusine indica* L.), wild oat (*Avena fatua* L.), johnsongrass (*Sorghum halepense* L.), quackgrass (*Agropyron repens* L.), alexandergrass (*Brachiaria plantaginea*), guineagrass (*Panicum maximum* Jacq.), paragrass (*Panicum purpurascens*), sprangletop (*Leptochloa chinensis*), red sprangletop (*Leptochloa panicea*), annual bluegrass (*Poa annua* L.), black grass (*Alopecurus myosuroides* Huds.), cholorado bluestem (*Agropyron tsukushiense* (Honda) Ohwi), broadleaf signalgrass (*Brachiaria platyphylla* Nash), southern sandbur (*Cenchrus echinatus* L.), italian ryegrass (*Lolium multiflorum* Lam.), and bermudagrass (*Cynodon dactylon* Pers.); cyperaceae such as rice flatsedge (*Cyperus iria* L.), purple nutsedge (*Cyperus rotundus* L.), yellow nutsedge (*Cyperus esculentus* L.), Japanese bulrush (*Scirpus juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon waparo (*Sagittaria pygmaea*), arrow-head (*Sagittaria trifolia*), and narrowleaf waterplantain (*Alisma canaliculatum*); pontederiaceae such as monochoria (*Monochoria vaginalis*), and monochoria species (*Monochoria korsakowii*); scrophulariaceae such as false pimpernel (*Lindernia pyxidaria*), and abunome (*Dopatrium junceum*); lythraceae such as toothcup (*Rotala india*), and red stem (*Ammannia multiflora*); elatinaceae such as long stem waterwort (*Elatine triandra* SCHK.); malvaceae such as velvetleaf (*Abutilon theophrasti* MEDIC.), and prickly *sida* (*Sida spinosa* L.); compositae such as common cocklebur (*Xanthium strumarium* L.), common ragweed (*Ambrosia elatior* L.), thistle (*Breea setosa* (BIEB.) KITAM.), hairy galinsoga (*Galinsoga ciliata* Blake), wild chamomile (*Matricaria chamomilla* L.); solanaceae such as black nightshade (*Solanum nigrum* L.), and jimsonweed (*Datura stramonium*); amaranthaceae such as slender amaranth (*Amaranthus viridis* L.), and redroot pigweed (*Amaranthus retroflexus* L.); polygonaceeae such as pale smartweed (*Polygonum lapathifolium* L.), ladysthumb (*Polygonum persicaria* L.), wild buckwheat (*Polygonum convolvulus* L.), and knotweed (*Polygonum aviculare* L.); cruciferae such as flexuous bittercress (*Cardamine flexuosa* WITH.), shepherd's-purse (*Capsella bursa-pastoris* Medik.), and indian mustard (*Brassica juncea* Czern.); convolvulaceae such as tall morningglory (*Ipomoea purpurea* L.), field bindweed (*Calystegia arvensis* L.), and ivyleaf morningglory (*Ipomoea hederacea* Jacq.); Chenopodiaceae such as common lambsquarters (*Chenopodium album* L.), and mexican burningbush (*Kochia scoparia* Schrad.); Portulacaceae such as common purslane (*Portulaca oleracea* L.); leguminosae such as sicklepod (*Cassia obtusifolia* L.); caryophyllaceae such as common chickweed (*Stellaria media* L.); labiatae such as henbit (*Lamium amplexicaule* L.); rubiaceae such as catchweed (*Galium spurium* L.); euphorbiaceae such as threeseeded copperleaf (*Acalypha australis* L.); and Commelinaceae such as common dayflower (*Commelina communis* L.).

Therefore, they can be effectively used for selectively controlling noxious weeds or nonselectively controlling noxious weeds in cultivation of useful crops such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), rye (*Secale cereale* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawngrass (*Zoysia japonica* stend), peanut (*Arachis hypogaea* L.), flax (*Linum usitatissimum* L.), tobacco (*Nicotiana tabacum* L.), and coffee (*Coffea* spp.). Particularly, the compounds of the present invention are effectively used for selectively controlling noxious weeds in cultivation of corn, soybean, cotton, wheat, rice, rape, sunflower, sugar beet, sugar cane, japanese lawngrass, peanut, flax, tobacco, coffee, and the like, and among these, especially corn, wheat, rice, japanese lawngrass and the like. In cultivation of such crop plants, for example, in cultivation of corn, among the above-mentioned noxious weeds, gramineae and malvaceae are, for example, typical noxious weeds, and green foxtail, guineagrass and velvet leaf belonging thereto may, for example, be mentioned as hardly controllable weeds. While having safety to crop plants, the compounds of the present invention can be used particularly effectively not only to control the above noxious weeds but also to control hardly controllable noxious weeds such as green foxtail, guineagrass and velvet leaf.

The compound of the present invention may be mixed with various agricultural additives and applied in the form of various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

The additives to be used for the formulation include, for example, a solid carrier such as diatomaceous earth, slaked lime, calcium carbonate, talc, white carbon, kaoline, bentonite, a mixture of kaolinite and sericite, clay, sodium carbonate, sodium bicarbonate, mirabilite, zeolite or starch; a solvent such as water, toluene, xylene, solvent naphtha, dioxane, acetone, isophorone, methyl isobutyl ketone, chlorobenzene, cyclohexane, dimethyl sulfoxide, N,N-dimethylformamide, dimethylacetamide, N-methyl-2-pyrrolidone or an alcohol; an anionic surfactant such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonate condensed with formaldehyde or an alkylnaphthalene sulfonate condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the compound of the present invention to such various additives may be from 0.1:99.9 to 95:5, preferably from 0.2:99.8 to 85:15.

The dose of the herbicide containing the compound of the present invention can not generally be defined, as it varies depending upon the weather conditions, the soil conditions, the type of the formulation, the type of the weeds to be controlled, the application season, etc. However, it is usually applied in an amount of the compound of the present invention of from 0.1 to 5,000 g, preferably from 0.5 to 1,000 g, more preferably from 1 to 500 g, per hectare. The present invention includes such a method for controlling undesired weeds, by such applications of the herbicide.

Further, the herbicide containing compound of the present invention may be mixed with or may be used in combination with other agricultural chemicals, fertilizers or phytotoxicity-reducing agents, whereby synergistic effects or activities may sometimes be obtained. Such other agricultural chemicals include, for example, a herbicide, a fungicide, an antibiotic, a plant hormone and an insecticide. Especially, with a mixed herbicidal composition having a compound of the present invention mixed with or used in combination with one or more active compounds of other herbicides, the range of weeds to be controlled, the time of application of the composition, the herbicidal activities, etc. may be improved to preferred directions. The compound of the present invention and the active compounds of other herbicides may separately be formulated so that they may be mixed for use at the time of application, or they may be formulated together. The present invention includes such a mixed herbicidal composition.

The mixing ratio of the compound of the present invention to the active compounds of other herbicides can not generally be defined, since it varies depending upon the weather conditions, the soil conditions, the types of formulations, the application time, the application method, etc., but the other herbicides are mixed in an amount of from 0.001 to 10,000 parts by weight, preferably from 0.01 to 1,000 parts by weight per one type of the active compound, based on 1 part by weight of the compound of the present invention. Further, the dose for the application is such that the total amount of the active compounds is from 0.1 to 10,000 g, preferably from 0.2 to 5,000 g, more preferably from 10 to 3,000 g, per hectare. The present invention includes a method for controlling undesired weeds by application of such a mixed herbicidal composition.

Another herbicidally active compound includes, for example, the following compounds (common names including ones under application for approval by ISO). Even when not specifically mentioned here, in a case where such compounds have salts, alkyl esters, etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol or chlorflurenol-methyl.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton or trietazine; a triazine type such as simazine, atrazine, atratone, simetryn, prometryn, dimethametryn, hexazinone, metribuzin, terbuthylazine, cyanazine, ametryn, cybutryne, triaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl(HC-252), fluoroglycofen-ethyl or fluoroglycofen; a cyclic imide type such as chlorphthalim, flumioxazin, flumiclorac, flumiclorac-pentyl, cinidon-ethyl or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, flupoxam, fluazolate, profluazol, pyraclonil, flufenpyr-ethyl or bencarbazone.

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone (BAS-670H) or pyrasulfotole; and others such as amitrole, fluridone, flurtamone, diflufenican, methoxyphenone, clomazone, sulcotrione, mesotrione, tembotrione, tefuryltrione (AVH-301), isoxaflutole, difenzoquat, difenzoquat-metilsulfate, isoxachlortole, benzobicyclon, picolinafen or beflubutamid.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; or others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chiorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, TH-547, a compound disclosed in WO2005092104; a triazolopyrimidinesulfonamide type such as flumetsulam, metosulam, diclosulam, cloransulam-methyl, florasulam or penoxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid, pyrimisulfan (KUH-021); a sulfonylaminocarbonyltriazolinone type such as flucarbazone, flucarbazone-sodium, propoxycarbazone-sodium or propoxycarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochloror dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone (KIH-485), dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid, nonanoic acid, fosamine, fosamine-ammonium, pinoxaden, HOK-201, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras*.

Examples of preferred embodiments of the present invention are shown below, but the present invention is by no means restricted thereto.

(1) A benzoylpyrazole compound of the above formula (I) or its salt, wherein $R^1$ is alkyl, $R^2$ is a hydrogen atom or alkyl, $R^3$ is alkyl, $R^4$ is alkyl, $R^5$ is alkyl substituted by one $Y^1$, alkoxy substituted by one $Y^2$, or alkoxycarbonyl, $R^6$ is alkylsulfonyl, A is alkylene substituted by one alkyl, $Y^1$ is alkoxy or haloalkoxy, and $Y^2$ is alkoxy.

(2) The benzoylpyrazole compound or its salt of the above (1), wherein $R^2$ is a hydrogen atom and $R^5$ is alkoxy substituted by one alkoxy.

(3) The benzoylpyrazole compound or its salt of the above (1), wherein $R^1$ is methyl, $R^2$ is a hydrogen atom, $R^3$ is methyl, $R^4$ is methyl, $R^5$ is 2-methoxyethoxy, $R^6$ is methylsulfonyl, and A is the formula (a-1):

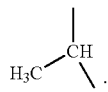

(4) The benzoylpyrazole compound or its salt of the above (1), wherein $R^1$ is methyl, $R^2$ is a hydrogen atom, $R^3$ is ethyl, $R^4$ is methyl, $R^5$ is 2-methoxyethoxy, $R^6$ is methylsulfonyl, and A is the formula (a-1):

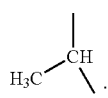

(5) The benzoylpyrazole compound or its salt of the above (1), wherein $R^1$ is methyl, $R^2$ is a hydrogen atom, $R^3$ is isopropyl, $R^4$ is methyl, $R^5$ is 2-methoxyethoxy, $R^6$ is methylsulfonyl, and A is the formula (a-1):

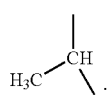

(6) The benzoylpyrazole compound or its salt of the above (1), wherein $R^1$ is methyl, $R^2$ is a hydrogen atom, $R^3$ is ethyl, $R^4$ is methyl, $R^5$ is methoxymethyl, $R^6$ is methylsulfonyl, and A is the formula (a-1):

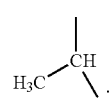

(7) A herbicidal composition comprising a benzoylpyrazole compound of the above formula (I) or its salt, and an agricultural adjuvant.

(8) A method for controlling undesired plants or inhibiting their growth, which comprises applying a herbicidally effective amount of the benzoylpyrazole compound of the above formula (I) or its salt to the undesired plants or to a place where they grow.

(9) The method of the above (8), wherein the undesired plants are controlled or their growth is inhibited in a corn field.

(10) The method of the above (9), wherein the corn is a transformed one.

(11) The method of the above (8), wherein the undesired plants are controlled or their growth is inhibited in a wheat, a barley, or a rye field.

(12) The method of the above (8), wherein the undesired plants are controlled or their growth is inhibited in a rice field.

(13) The method of the above (8), wherein the undesired plants are controlled or their growth is inhibited in a non-agricultural field.

(14) Use of a benzoylpyrazole compound of the above formula (I) or its salt, as an active ingredient for a selective herbicide in a corn field.

Now, the present invention will be described in further detail with reference to Examples. However, it should be understood that the present invention is by no means restricted to such specific Examples.

A Preparation Example for a compound of the present invention is described below.

Preparation Example

Preparation of 1-(4-(3-(2-methoxyethoxy)-2-methyl-4-(methylsulfonyl)benzoyl)-1-methyl-1H-pyrazol-5-yloxy)ethyl ethylcarbonate (compound No. 2 as described hereinafter)

(1) Methyl 3-hydroxy-2-methyl-4-nitrobenzoate (1.55 g) and 2-chloroethyl methyl ether (1.8 g) were dissolved in anhydrous DMF (20 mL), and potassium carbonate (1.25 g) and potassium iodide (300 mg) were added, followed by stirring at 90° C. for 20 hours. To the reaction mixture, ethyl acetate (200 mL) was added, followed by washing twice with saturated brine. The organic layer was dried over anhydrous sodium sulfate and then concentrated under reduced pressure to obtain methyl 3-(2-methoxyethoxy)-2-methyl-4-nitrobenzoate (2.1 g) as pale yellow solid.

$^1$H-NMR (400 MHz CDCl$_3$ δ ppm): 2.54 (3H, s), 3.39 (3H, s), 3.70 (2H, m), 3.91 (3H, m), 4.11 (2H, m), 7.59 (1H, d, J=8.0 Hz), 7.64 (1H, d, J=8.0 Hz).

(2) Methyl 3-(2-methoxyethoxy)-2-methyl-4-nitrobenzoate (31 g) was dissolved in anhydrous DMF (300 mL), and sodium thiomethoxide (purity: 95%, 8.92 g) was added at room temperature, followed by stirring for 45 minutes. To the reaction mixture, ethyl acetate (400 mL) was added and washed once with 1 N hydrochloric acid (150 mL) and washed twice with saturated brine. The organic layer was dried over anhydrous sodium sulfate, and the solvent was distilled off under reduced pressure to obtain methyl 3-(2-methoxyethoxy)-2-methyl-4-(methylthio)benzoate (30 g) as a solid.

$^1$H-NMR (400 MHz CDCl$_3$ δ ppm): 2.24 (3H, s), 2.53 (3H, s), 3.48 (3H, s), 3.78 (2H, m), 3.86 (3H, s), 4.01 (2H, m), 6.96 (1H, d, J=8.4 Hz), 7.68 (1H, d, J=8.4 Hz).

(3) Methyl 3-(2-methoxyethoxy)-2-methyl-4-(methylthio)benzoate (30 g) was dissolved in acetic acid (300 mL), and sodium tungstate dihydrate (0.08 equivalent, 2.9 g) was added. Hydrogen peroxide (30%, 38 mL) was dropwise added thereto at room temperature over a period of 10 minutes. The reaction mixture was stirred at room temperature for three hours, and then, ethyl acetate (300 mL) and hexane (300 mL) were added, followed by washing three times with saturated brine. The organic layer was washed with a saturated sodium hydrogen carbonate aqueous solution and then dried over anhydrous sodium sulfate. The solvent was distilled off under reduced pressure to obtain methyl 3-(2-methoxyethoxy)-2-methyl-4-(methylsulfonyl)benzoate (26 g).

$^1$H-NMR (400 MHz CDCl$_3$ δ ppm): 2.54 (3H, s), 3.26 (3H, s), 3.46 (3H, s), 3.79 (2H, m), 3.91 (3H, s), 4.19 (2H, m), 7.71 (1H, d, J=8.4 Hz), 7.84 (1H, d, J=8.4 Hz)

(4) Methyl 3-(2-methoxyethoxy)-2-methyl-4-(methylsulfonyl)benzoate (26 g) was dissolved in methanol (200 mL), and a 20% NaOH aqueous solution (50 mL) was added at room temperature. After stirring for one hour, methanol was distilled off under reduced pressure. To the residue, 2N hydrochloric acid (100 mL) was added, followed by extraction with ethyl acetate (500 mL). The organic layer was washed with saturated brine and dried over anhydrous sodium sulfate, and then, the solvent was distilled off under reduced pressure. To the residue, a mixed solvent (ethyl acetate:hexane=1:1, 50 mL) was added, and the mixture was left to stand at 5° C. for 12 hours. The obtained crystals were collected by filtration to obtain 3-(2-methoxyethoxy)-2-methyl-4-(methylsulfonyl)benzoic acid (19.5 g).

$^1$H-NMR (400 MHz CDCl$_3$ δ ppm): 2.63 (3H, s), 3.31 (3H, s), 3.49 (3H, s), 3.83 (2H, m), 4.23 (2H, m), 7.91 (2H, s).

(5) 3-(2-methoxyethoxy)-2-methyl-4-(methylsulfonyl)benzoic acid (10 g) was dissolved in chloroform (200 mL), and oxalyl chloride (6.0 mL) and DMF (catalytic amount) were added at room temperature. After stirring for one hour, chloroform and unreacted oxalyl chloride were distilled off under reduced pressure. To the residue, 1-methyl-1H-pyrazol-5-ol (3.8 g), 4-dimethylaminopyridine (8.5 g), tetrahydrofuran (200 mL) and triethylamine (7.3 mL) were added, followed by refluxing under heating for one hour. Then, to the cooled reaction mixture, ethyl acetate (50 mL) was added and washed sequentially with saturated brine and 0.30N hydrochloric acid (200 mL) and dried over anhydrous sodium sulfate. The solvent was distilled off under reduced pressure, and the residue was washed with hexane to obtain 3-(2-methoxyethoxy)-2-methyl-4-(methylsulfonyl)benzoic acid 1-methyl-1H-pyrazol-5-yl ester (7.8 g).

$^1$H-NMR (400 MHz CDCl$_3$ δ ppm): 2.66 (3H, s), 3.32 (3H, s), 3.49 (3H, s), 3.81 (3H, s), 3.83 (2H, m), 4.25 (2H, m), 6.28 (1H, d, J=2.0 Hz), 7.49 (1H, d, J=2.0 Hz), 7.99 (2H, s).

(6) 3-(2-methoxyethoxy)-2-methyl-4-(methylsulfonyl)benzoic acid 1-methyl-1H-pyrazol-5-yl ester (7.8 g) was dissolved in acetonitrile (100 mL), and triethylamine (7.9 mL) and acetone cyanohydrin (0.87 mL) were added at room temperature. After stirring for 6 hours, the solvent was distilled off under reduced pressure. To the residue, ethyl acetate (100 mL) was added, followed by washing sequentially with 1N hydrochloric acid (50 mL), water and saturated brine, and drying over anhydrous sodium sulfate. The solvent was distilled off under reduced pressure, and the residue was washed with hexane to obtain 4-(3-(2-methoxyethoxy)-2-methyl-4-(methylsulfonyl)benzoyl)-1-methyl-1H-pyrazol-5-ol (4.2 g).

$^1$H-NMR (400 MHz CDCl$_3$ δ ppm): 2.41 (3H, s), 3.31 (3H, s), 3.48 (3H, s), 3.73 (3H, s), 3.82 (2H, m), 4.26 (2H, m), 7.34 (1H, s), 7.36 (1H, d, J=8.4 Hz), 7.94 (1H, d, J=8.4 Hz).

(7) 4-(3-(2-methoxyethoxy)-2-methyl-4-(methylsulfonyl)benzoyl)-1-methyl-1H-pyrazol-5-ol (4.2 g) was dissolved in acetone (50 mL), and potassium carbonate (5.5 g) and 1-chloroethyl ethyl carbonate (9.1 g) were added, followed by refluxing under heating for 4 hours. Then, sodium iodide (10 g) was added, followed by further refluxing for one hour. After being left to cool, the reaction mixture was dissolved in ethyl acetate (100 mL), and water was added. This mixed solvent system was extracted three times with ethyl acetate, and the organic layer was washed with saturated brine and then dried over anhydrous sodium sulfate. The solvent was distilled off under reduced pressure, and the residue was purified by silica gel column chromatography (developing solvent: ethyl acetate:hexane=1:1), and the solvent was distilled off to obtain a solid. To the obtained solid, a mixed solvent (hexane:ethyl acetate=7:3, 50 mL) was added, and the mixture was left to stand at 5° C. for 12 hours. The obtained crystals were collected by filtration to obtain the desired product (2.0 g) having a melting point of 120° C.

Now, typical examples of the compounds represented by the above formula (I) are shown in Table 1, and their $^1$H-NMR spectrum data are shown in Table 2. These compounds can be prepared in accordance with the above Preparation Example or the Above Various Processes for production of the compounds of the present invention. In Tables 1 and 2, No. represents the compound number. Further, in Table 1, Me represents a methyl group, Et an ethyl group, n-Pr a normal-propyl group, i-Pr an isopropyl group, n-Bu a normal butyl group and t-Bu a tertiary butyl group. Further, the left side of -A- is bonded to the pyrazole side, and the right side of -A- is bonded to the carbonate side.

TABLE 1

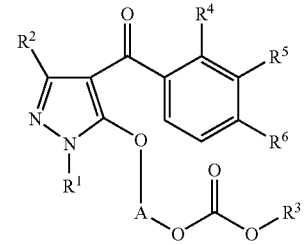

(I)

| No. | R$^1$ | R$^2$ | R$^3$ | R$^4$ | R$^5$ | R$^6$ | —A— |
|---|---|---|---|---|---|---|---|
| 1 | Me | H | Me | Me | OCH$_2$CH$_2$OMe | SO$_2$Me | —CH(Me)— |
| 2 | Me | H | Et | Me | OCH$_2$CH$_2$OMe | SO$_2$Me | —CH(Me)— |
| 3 | Et | H | Et | Me | OCH$_2$CH$_2$OMe | SO$_2$Me | —CH(Me)— |
| 4 | Me | H | i-Pr | Me | OCH$_2$CH$_2$OMe | SO$_2$Me | —CH(Me)— |
| 5 | Me | H | Et | Me | OCH$_2$CH$_2$OMe | SO$_2$Me | —C(Me)$_2$— |
| 6 | Me | H | Et | Me | OCH$_2$CF$_3$ | SO$_2$Me | —CH(Me)— |
| 7 | Me | H | Et | Me | CH$_2$OMe | SO$_2$Me | —CH(Me)— |
| 8 | Me | H | Et | Cl | CH$_2$OMe | SO$_2$Me | —CH(Me)— |
| 9 | n-Bu | H | Et | Me | OCH$_2$CH$_2$OMe | SO$_2$Me | —CH(Me)— |
| 10 | t-Bu | H | Et | Me | OCH$_2$CH$_2$OMe | SO$_2$Me | —CH(Me)— |
| 11 | Me | Me | Et | Me | OCH$_2$CH$_2$OMe | SO$_2$Me | —CH(Me)— |
| 12 | Me | H | Et | Me | OCH$_2$CH$_2$OMe | SO$_2$Me | —C(Me)(Et)— |
| 13 | Me | H | Et | Me | OCH$_2$CH$_2$OMe | SO$_2$Me | —CH(Et)— |
| 14 | Me | H | Et | Me | OCH$_2$CH$_2$OMe | SO$_2$Me | —CH(i-Pr)— |
| 15 | Me | H | Et | Me | CH$_2$OCH$_2$CF$_3$ | SO$_2$Me | —CH(Me)— |
| 16 | Et | H | Et | Cl | C(O)OMe | SO$_2$Me | —CH(Me)— |
| 17 | Me | H | Et | Cl | OCH$_2$CH$_2$OMe | SO$_2$Me | —CH(Me)— |
| 18 | i-Pr | H | Et | Me | OCH$_2$CH$_2$OMe | SO$_2$Me | —CH(Me)— |

TABLE 1-continued

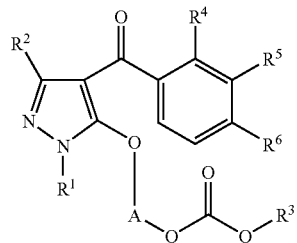

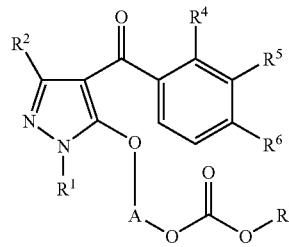

| No. | R¹ | R² | R³ | R⁴ | R⁵ | R⁶ | —A— |
|---|---|---|---|---|---|---|---|
| 19 | Me | H | n-Pr | Me | OCH₂CH₂OMe | SO₂Me | —CH(Me)— |
| 20 | Me | H | n-Bu | Me | OCH₂CH₂OMe | SO₂Me | —CH(Me)— |
| 21 | Me | H | Et | Me | C(O)OMe | SO₂Me | —CH(Me)— |
| 22 | Me | H | Me | Me | OCH₂CH₂OMe | SO₂Me | —C(Me)₂— |
| 23 | Et | H | Et | Me | OCH₂CH₂OMe | SO₂Me | —C(Me)₂— |
| 24 | Me | H | i-Pr | Me | OCH₂CH₂OMe | SO₂Me | —C(Me)₂— |
| 25 | i-Pr | Me | Et | Me | OCH₂CH₂OMe | SO₂Me | —C(Me)₂— |
| 26 | Me | H | n-Pr | Me | OCH₂CH₂OMe | SO₂Me | —C(Me)₂— |
| 27 | Me | H | n-Bu | Me | OCH₂CH₂OMe | SO₂Me | —C(Me)₂— |
| 28 | Me | H | Et | Me | OCH₂CH₂OMe | SO₂Me | —C(Me)₂— |
| 29 | Et | H | Et | Cl | OCH₂CH₂OMe | SO₂Me | —CH(Me)— |
| 30 | t-Bu | H | Et | Cl | OCH₂CH₂OMe | SO₂Me | —CH(Me)— |
| 31 | Me | Me | Et | Cl | OCH₂CH₂OMe | SO₂Me | —CH(Me)— |
| 32 | Me | H | Me | Me | OCH₂CH₂OMe | SO₂Et | —CH(Me)— |
| 33 | Me | H | Et | Me | OCH₂CH₂OMe | SO₂Et | —CH(Me)— |
| 34 | Et | H | Et | Me | OCH₂CH₂OMe | SO₂Et | —CH(Me)— |
| 35 | Me | H | i-Pr | Me | OCH₂CH₂OMe | SO₂Et | —CH(Me)— |
| 36 | Me | H | Et | Me | OCH₂CH₂OMe | SO₂Et | —C(Me)₂— |
| 37 | Me | H | Et | Me | OCH₂CF₃ | SO₂Et | —CH(Me)— |
| 38 | Me | H | Et | Me | CH₂OMe | SO₂Et | —CH(Me)— |
| 39 | Me | H | Et | Cl | CH₂OMe | SO₂Et | —CH(Me)— |
| 40 | n-Bu | H | Et | Me | OCH₂CH₂OMe | SO₂Et | —CH(Me)— |
| 41 | t-Bu | H | Et | Me | OCH₂CH₂OMe | SO₂Et | —CH(Me)— |
| 42 | Me | Me | Et | Me | OCH₂CH₂OMe | SO₂Et | —CH(Me)— |
| 43 | Me | H | Et | Me | OCH₂CH₂OMe | SO₂Et | —C(Me)(Et)— |
| 44 | Me | H | Et | Me | OCH₂CH₂OMe | SO₂Et | —CH(Et)— |
| 45 | Me | H | Et | Me | OCH₂CH₂OMe | SO₂Et | —CH(i-Pr)— |
| 46 | Me | H | Et | Me | OCH₂CH₂CF₃ | SO₂Et | —CH(Me)— |
| 47 | Et | H | Et | Cl | C(O)OMe | SO₂Et | —CH(Me)— |
| 48 | Me | H | Et | Cl | OCH₂CH₂OMe | SO₂Et | —CH(Me)— |
| 49 | i-Pr | Me | Et | Me | OCH₂CH₂OMe | SO₂Et | —CH(Me)— |
| 50 | Me | H | n-Pr | Me | OCH₂CH₂OMe | SO₂Et | —CH(Me)— |
| 51 | Me | H | n-Bu | Me | OCH₂CH₂OMe | SO₂Et | —CH(Me)— |
| 52 | Me | H | Et | Me | C(O)OMe | SO₂Et | —CH(Me)— |
| 53 | Me | H | Me | Me | OCH₂CH₂OMe | SO₂Et | —CH(Me)— |
| 54 | Et | H | Et | Me | OCH₂CH₂OMe | SO₂Et | —C(Me)₂— |
| 55 | Me | H | i-Pr | Me | OCH₂CH₂OMe | SO₂Et | —CH(Me)— |
| 56 | Me | H | Me | Br | OCH₂CH₂OMe | SO₂Me | —CH(Me)— |
| 57 | Me | H | Et | Br | OCH₂CH₂OMe | SO₂Me | —CH(Me)— |
| 58 | Et | H | Et | Br | OCH₂CH₂OMe | SO₂Me | —CH(Me)— |
| 59 | Me | H | i-Pr | Br | OCH₂CH₂OMe | SO₂Me | —CH(Me)— |
| 60 | Me | H | Et | Br | OCH₂CH₂OMe | SO₂Me | —C(Me)₂— |
| 61 | Me | H | Et | Br | OCH₂CF₃ | SO₂Me | —CH(Me)— |
| 62 | Me | H | Et | Br | CH₂OMe | SO₂Me | —CH(Me)— |
| 63 | n-Bu | H | Et | Me | OCH₂CH₂OMe | SO₂Et | —CH(Me)— |
| 64 | t-Bu | H | i-Pr | Me | OCH₂CH₂OMe | SO₂Et | —CH(Me)— |
| 65 | Me | Me | i-Pr | Me | OCH₂CH₂OMe | SO₂Me | —CH(Me)— |
| 66 | Me | Et | Me | Me | OCH₂CH₂OMe | SO₂Me | —CH(Me)— |
| 67 | Me | Et | Et | Me | OCH₂CH₂OMe | SO₂Me | —CH(Me)— |
| 68 | Me | Et | i-Pr | Me | OCH₂CH₂OMe | SO₂Me | —CH(Me)— |
| 69 | Me | Et | n-Pr | Me | OCH₂CH₂OMe | SO₂Me | —CH(Me)— |
| 70 | Me | Et | n-Bu | Me | OCH₂CH₂OMe | SO₂Me | —CH(Me)— |
| 71 | Et | Et | Me | Me | OCH₂CH₂OMe | SO₂Me | —CH(Me)— |
| 72 | Et | Et | Et | Me | OCH₂CH₂OMe | SO₂Me | —CH(Me)— |
| 73 | Et | Et | i-Pr | Me | OCH₂CH₂OMe | SO₂Me | —CH(Me)— |
| 74 | Et | Et | n-Pr | Me | OCH₂CH₂OMe | SO₂Me | —CH(Me)— |
| 75 | Et | Et | n-Bu | Me | OCH₂CH₂OMe | SO₂Me | —CH(Me)— |
| 76 | i-Pr | Et | Me | Me | OCH₂CH₂OMe | SO₂Me | —CH(Me)— |
| 77 | i-Pr | Et | Et | Me | OCH₂CH₂OMe | SO₂Me | —CH(Me)— |
| 78 | i-Pr | Et | i-Pr | Me | OCH₂CH₂OMe | SO₂Me | —CH(Me)— |
| 79 | i-Pr | Et | n-Pr | Me | OCH₂CH₂OMe | SO₂Me | —CH(Me)— |
| 80 | i-Pr | Et | n-Bu | Me | OCH₂CH₂OMe | SO₂Me | —CH(Me)— |
| 81 | n-Pr | Et | Me | Me | OCH₂CH₂OMe | SO₂Me | —CH(Me)— |
| 82 | n-Pr | Et | Et | Me | OCH₂CH₂OMe | SO₂Me | —CH(Me)— |
| 83 | n-Pr | Et | i-Pr | Me | OCH₂CH₂OMe | SO₂Me | —CH(Me)— |
| 84 | n-Pr | Et | n-Pr | Me | OCH₂CH₂OMe | SO₂Me | —CH(Me)— |
| 85 | n-Pr | Et | n-Bu | Me | OCH₂CH₂OMe | SO₂Me | —CH(Me)— |
| 86 | n-Bu | Et | Me | Me | OCH₂CH₂OMe | SO₂Me | —CH(Me)— |
| 87 | n-Bu | Et | Et | Me | OCH₂CH₂OMe | SO₂Me | —CH(Me)— |
| 88 | n-Bu | Et | i-Pr | Me | OCH₂CH₂OMe | SO₂Me | —CH(Me)— |
| 89 | n-Bu | Et | n-Pr | Me | OCH₂CH₂OMe | SO₂Me | —CH(Me)— |
| 90 | n-Bu | Et | n-Bu | Me | OCH₂CH₂OMe | SO₂Me | —CH(Me)— |
| 91 | t-Bu | Et | Me | Me | OCH₂CH₂OMe | SO₂Me | —CH(Me)— |
| 92 | t-Bu | Et | Et | Me | OCH₂CH₂OMe | SO₂Me | —CH(Me)— |
| 93 | t-Bu | Et | i-Pr | Me | OCH₂CH₂OMe | SO₂Me | —CH(Me)— |
| 94 | t-Bu | Et | n-Pr | Me | OCH₂CH₂OMe | SO₂Me | —CH(Me)— |
| 95 | t-Bu | Et | n-Bu | Me | OCH₂CH₂OMe | SO₂Me | —CH(Me)— |
| 96 | Me | Et | Me | Cl | OCH₂CH₂OMe | SO₂Me | —CH(Me)— |
| 97 | Me | Et | Et | Cl | OCH₂CH₂OMe | SO₂Me | —CH(Me)— |
| 98 | Me | Et | i-Pr | Cl | OCH₂CH₂OMe | SO₂Me | —CH(Me)— |
| 99 | Me | Et | n-Pr | Cl | OCH₂CH₂OMe | SO₂Me | —CH(Me)— |
| 100 | Me | Et | n-Bu | Cl | OCH₂CH₂OMe | SO₂Me | —CH(Me)— |
| 101 | Et | Et | Me | Cl | OCH₂CH₂OMe | SO₂Me | —CH(Me)— |
| 102 | Et | Et | Et | Cl | OCH₂CH₂OMe | SO₂Me | —CH(Me)— |
| 103 | Et | Et | i-Pr | Cl | OCH₂CH₂OMe | SO₂Me | —CH(Me)— |
| 104 | Et | Et | n-Pr | Cl | OCH₂CH₂OMe | SO₂Me | —CH(Me)— |
| 105 | Et | Et | n-Bu | Cl | OCH₂CH₂OMe | SO₂Me | —CH(Me)— |
| 106 | i-Pr | Et | Me | Cl | OCH₂CH₂OMe | SO₂Me | —CH(Me)— |
| 107 | i-Pr | Et | Et | Cl | OCH₂CH₂OMe | SO₂Me | —CH(Me)— |
| 108 | i-Pr | Et | i-Pr | Cl | OCH₂CH₂OMe | SO₂Me | —CH(Me)— |
| 109 | i-Pr | Et | n-Pr | Cl | OCH₂CH₂OMe | SO₂Me | —CH(Me)— |
| 110 | i-Pr | Et | n-Bu | Cl | OCH₂CH₂OMe | SO₂Me | —CH(Me)— |
| 111 | n-Pr | Et | Me | Cl | OCH₂CH₂OMe | SO₂Me | —CH(Me)— |
| 112 | n-Pr | Et | Et | Cl | OCH₂CH₂OMe | SO₂Me | —CH(Me)— |
| 113 | n-Pr | Et | i-Pr | Cl | OCH₂CH₂OMe | SO₂Me | —CH(Me)— |
| 114 | n-Pr | Et | n-Pr | Cl | OCH₂CH₂OMe | SO₂Me | —CH(Me)— |
| 115 | n-Pr | Et | n-Bu | Cl | OCH₂CH₂OMe | SO₂Me | —CH(Me)— |
| 116 | n-Bu | Et | Me | Cl | OCH₂CH₂OMe | SO₂Me | —CH(Me)— |
| 117 | n-Bu | Et | Et | Cl | OCH₂CH₂OMe | SO₂Me | —CH(Me)— |
| 118 | n-Bu | Et | i-Pr | Cl | OCH₂CH₂OMe | SO₂Me | —CH(Me)— |
| 119 | n-Bu | Et | n-Pr | Cl | OCH₂CH₂OMe | SO₂Me | —CH(Me)— |
| 120 | n-Bu | Et | n-Bu | Cl | OCH₂CH₂OMe | SO₂Me | —CH(Me)— |
| 121 | t-Bu | Et | Me | Cl | OCH₂CH₂OMe | SO₂Me | —CH(Me)— |
| 122 | t-Bu | Et | Et | Cl | OCH₂CH₂OMe | SO₂Me | —CH(Me)— |
| 123 | t-Bu | Et | i-Pr | Cl | OCH₂CH₂OMe | SO₂Me | —CH(Me)— |
| 124 | t-Bu | Et | n-Pr | Cl | OCH₂CH₂OMe | SO₂Me | —CH(Me)— |
| 125 | t-Bu | Et | n-Bu | Cl | OCH₂CH₂OMe | SO₂Me | —CH(Me)— |
| 126 | Me | Et | Me | Me | OCH₂CF₃ | SO₂Me | —CH(Me)— |
| 127 | Me | Et | Et | Me | OCH₂CF₃ | SO₂Me | —CH(Me)— |
| 128 | Me | Et | i-Pr | Me | OCH₂CF₃ | SO₂Me | —CH(Me)— |
| 129 | Me | Et | n-Pr | Me | OCH₂CF₃ | SO₂Me | —CH(Me)— |
| 130 | Me | Et | n-Bu | Me | OCH₂CF₃ | SO₂Me | —CH(Me)— |
| 131 | Et | Et | Me | Me | OCH₂CF₃ | SO₂Me | —CH(Me)— |
| 132 | Et | Et | Et | Me | OCH₂CF₃ | SO₂Me | —CH(Me)— |
| 133 | Et | Et | i-Pr | Me | OCH₂CF₃ | SO₂Me | —CH(Me)— |
| 134 | Et | Et | n-Pr | Me | OCH₂CF₃ | SO₂Me | —CH(Me)— |
| 135 | Et | Et | n-Bu | Me | OCH₂CF₃ | SO₂Me | —CH(Me)— |
| 136 | i-Pr | Et | Me | Me | OCH₂CF₃ | SO₂Me | —CH(Me)— |
| 137 | i-Pr | Et | Et | Me | OCH₂CF₃ | SO₂Me | —CH(Me)— |
| 138 | i-Pr | Et | i-Pr | Me | OCH₂CF₃ | SO₂Me | —CH(Me)— |
| 139 | i-Pr | Et | n-Pr | Me | OCH₂CF₃ | SO₂Me | —CH(Me)— |
| 140 | i-Pr | Et | n-Bu | Me | OCH₂CF₃ | SO₂Me | —CH(Me)— |
| 141 | n-Pr | Et | Me | Me | OCH₂CF₃ | SO₂Me | —CH(Me)— |
| 142 | n-Pr | Et | Et | Me | OCH₂CF₃ | SO₂Me | —CH(Me)— |
| 143 | n-Pr | Et | i-Pr | Me | OCH₂CF₃ | SO₂Me | —CH(Me)— |
| 144 | n-Pr | Et | n-Pr | Me | OCH₂CF₃ | SO₂Me | —CH(Me)— |
| 145 | n-Pr | Et | n-Bu | Me | OCH₂CF₃ | SO₂Me | —CH(Me)— |
| 146 | n-Bu | Et | Me | Me | OCH₂CF₃ | SO₂Me | —CH(Me)— |

TABLE 1-continued (I)

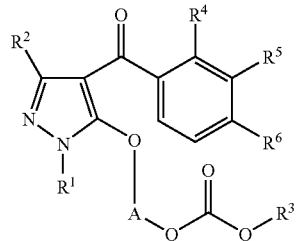

| No. | R¹ | R² | R³ | R⁴ | R⁵ | R⁶ | —A— |
|---|---|---|---|---|---|---|---|
| 147 | n-Bu | Et | Et | Me | OCH$_2$CF$_3$ | SO$_2$Me | —CH(Me)— |
| 148 | n-Bu | Et | i-Pr | Me | OCH$_2$CF$_3$ | SO$_2$Me | —CH(Me)— |
| 149 | n-Bu | Et | n-Pr | Me | OCH$_2$CF$_3$ | SO$_2$Me | —CH(Me)— |
| 150 | n-Bu | Et | n-Bu | Me | OCH$_2$CF$_3$ | SO$_2$Me | —CH(Me)— |
| 151 | t-Bu | Et | Me | Me | OCH$_2$CF$_3$ | SO$_2$Me | —CH(Me)— |
| 152 | t-Bu | Et | Et | Me | OCH$_2$CF$_3$ | SO$_2$Me | —CH(Me)— |
| 153 | t-Bu | Et | i-Pr | Me | OCH$_2$CF$_3$ | SO$_2$Me | —CH(Me)— |
| 154 | t-Bu | Et | n-Pr | Me | OCH$_2$CF$_3$ | SO$_2$Me | —CH(Me)— |
| 155 | t-Bu | Et | n-Bu | Me | OCH$_2$CF$_3$ | SO$_2$Me | —CH(Me)— |
| 156 | Me | Et | Me | Cl | OCH$_2$CF$_3$ | SO$_2$Me | —CH(Me)— |
| 157 | Me | Et | Et | Cl | OCH$_2$CF$_3$ | SO$_2$Me | —CH(Me)— |
| 158 | Me | Et | i-Pr | Cl | OCH$_2$CF$_3$ | SO$_2$Me | —CH(Me)— |
| 159 | Me | Et | n-Pr | Cl | OCH$_2$CF$_3$ | SO$_2$Me | —CH(Me)— |
| 160 | Me | Et | n-Bu | Cl | OCH$_2$CF$_3$ | SO$_2$Me | —CH(Me)— |
| 161 | Et | Et | Me | Cl | OCH$_2$CF$_3$ | SO$_2$Me | —CH(Me)— |
| 162 | Et | Et | Et | Cl | OCH$_2$CF$_3$ | SO$_2$Me | —CH(Me)— |
| 163 | Et | Et | i-Pr | Cl | OCH$_2$CF$_3$ | SO$_2$Me | —CH(Me)— |
| 164 | Et | Et | n-Pr | Cl | OCH$_2$CF$_3$ | SO$_2$Me | —CH(Me)— |
| 165 | Et | Et | n-Bu | Cl | OCH$_2$CF$_3$ | SO$_2$Me | —CH(Me)— |
| 166 | i-Pr | Et | Me | Cl | OCH$_2$CF$_3$ | SO$_2$Me | —CH(Me)— |
| 167 | i-Pr | Et | Et | Cl | OCH$_2$CF$_3$ | SO$_2$Me | —CH(Me)— |
| 168 | i-Pr | Et | i-Pr | Cl | OCH$_2$CF$_3$ | SO$_2$Me | —CH(Me)— |
| 169 | i-Pr | Et | n-Pr | Cl | OCH$_2$CF$_3$ | SO$_2$Me | —CH(Me)— |
| 170 | i-Pr | Et | n-Bu | Cl | OCH$_2$CF$_3$ | SO$_2$Me | —CH(Me)— |
| 171 | n-Pr | Et | Me | Cl | OCH$_2$CF$_3$ | SO$_2$Me | —CH(Me)— |
| 172 | n-Pr | Et | Et | Cl | OCH$_2$CF$_3$ | SO$_2$Me | —CH(Me)— |
| 173 | n-Pr | Et | i-Pr | Cl | OCH$_2$CF$_3$ | SO$_2$Me | —CH(Me)— |
| 174 | n-Pr | Et | n-Pr | Cl | OCH$_2$CF$_3$ | SO$_2$Me | —CH(Me)— |
| 175 | n-Pr | Et | n-Bu | Cl | OCH$_2$CF$_3$ | SO$_2$Me | —CH(Me)— |
| 176 | n-Bu | Et | Me | Cl | OCH$_2$CF$_3$ | SO$_2$Me | —CH(Me)— |
| 177 | n-Bu | Et | Et | Cl | OCH$_2$CF$_3$ | SO$_2$Me | —CH(Me)— |
| 178 | n-Bu | Et | i-Pr | Cl | OCH$_2$CF$_3$ | SO$_2$Me | —CH(Me)— |
| 179 | n-Bu | Et | n-Pr | Cl | OCH$_2$CF$_3$ | SO$_2$Me | —CH(Me)— |
| 180 | n-Bu | Et | n-Bu | Cl | OCH$_2$CF$_3$ | SO$_2$Me | —CH(Me)— |
| 181 | t-Bu | Et | Me | Cl | OCH$_2$CF$_3$ | SO$_2$Me | —CH(Me)— |
| 182 | t-Bu | Et | Et | Cl | OCH$_2$CF$_3$ | SO$_2$Me | —CH(Me)— |
| 183 | t-Bu | Et | i-Pr | Cl | OCH$_2$CF$_3$ | SO$_2$Me | —CH(Me)— |
| 184 | t-Bu | Et | n-Pr | Cl | OCH$_2$CF$_3$ | SO$_2$Me | —CH(Me)— |
| 185 | t-Bu | Et | n-Bu | Cl | OCH$_2$CF$_3$ | SO$_2$Me | —CH(Me)— |
| 186 | Me | Et | Me | Me | CH$_2$OMe | SO$_2$Me | —CH(Me)— |
| 187 | Me | Et | Et | Me | CH$_2$OMe | SO$_2$Me | —CH(Me)— |
| 188 | Me | Et | i-Pr | Me | CH$_2$OMe | SO$_2$Me | —CH(Me)— |
| 189 | Me | Et | n-Pr | Me | CH$_2$OMe | SO$_2$Me | —CH(Me)— |
| 190 | Me | Et | n-Bu | Me | CH$_2$OMe | SO$_2$Me | —CH(Me)— |
| 191 | Et | Et | Me | Me | CH$_2$OMe | SO$_2$Me | —CH(Me)— |
| 192 | Et | Et | Et | Me | CH$_2$OMe | SO$_2$Me | —CH(Me)— |
| 193 | Et | Et | i-Pr | Me | CH$_2$OMe | SO$_2$Me | —CH(Me)— |
| 194 | Et | Et | n-Pr | Me | CH$_2$OMe | SO$_2$Me | —CH(Me)— |
| 195 | Et | Et | n-Bu | Me | CH$_2$OMe | SO$_2$Me | —CH(Me)— |
| 196 | i-Pr | Et | Me | Me | CH$_2$OMe | SO$_2$Me | —CH(Me)— |
| 197 | i-Pr | Et | Et | Me | CH$_2$OMe | SO$_2$Me | —CH(Me)— |
| 198 | i-Pr | Et | i-Pr | Me | CH$_2$OMe | SO$_2$Me | —CH(Me)— |
| 199 | i-Pr | Et | n-Pr | Me | CH$_2$OMe | SO$_2$Me | —CH(Me)— |
| 200 | i-Pr | Et | n-Bu | Me | CH$_2$OMe | SO$_2$Me | —CH(Me)— |
| 201 | n-Pr | Et | Me | Me | CH$_2$OMe | SO$_2$Me | —CH(Me)— |
| 202 | n-Pr | Et | Et | Me | CH$_2$OMe | SO$_2$Me | —CH(Me)— |
| 203 | n-Pr | Et | i-Pr | Me | CH$_2$OMe | SO$_2$Me | —CH(Me)— |
| 204 | n-Pr | Et | n-Pr | Me | CH$_2$OMe | SO$_2$Me | —CH(Me)— |
| 205 | n-Pr | Et | n-Bu | Me | CH$_2$OMe | SO$_2$Me | —CH(Me)— |
| 206 | n-Bu | Et | Me | Me | CH$_2$OMe | SO$_2$Me | —CH(Me)— |
| 207 | n-Bu | Et | Et | Me | CH$_2$OMe | SO$_2$Me | —CH(Me)— |
| 208 | n-Bu | Et | i-Pr | Me | CH$_2$OMe | SO$_2$Me | —CH(Me)— |
| 209 | n-Bu | Et | n-Pr | Me | CH$_2$OMe | SO$_2$Me | —CH(Me)— |
| 210 | n-Bu | Et | n-Bu | Me | CH$_2$OMe | SO$_2$Me | —CH(Me)— |

TABLE 1-continued (I)

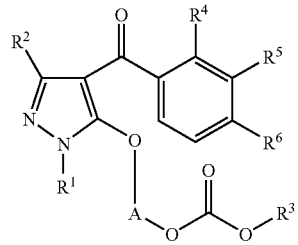

| No. | R¹ | R² | R³ | R⁴ | R⁵ | R⁶ | —A— |
|---|---|---|---|---|---|---|---|
| 211 | t-Bu | Et | Me | Me | CH$_2$OMe | SO$_2$Me | —CH(Me)— |
| 212 | t-Bu | Et | Et | Me | CH$_2$OMe | SO$_2$Me | —CH(Me)— |
| 213 | t-Bu | Et | i-Pr | Me | CH$_2$OMe | SO$_2$Me | —CH(Me)— |
| 214 | t-Bu | Et | n-Pr | Me | CH$_2$OMe | SO$_2$Me | —CH(Me)— |
| 215 | t-Bu | Et | n-Bu | Me | CH$_2$OMe | SO$_2$Me | —CH(Me)— |
| 216 | Me | Et | Me | Cl | CH$_2$OMe | SO$_2$Me | —CH(Me)— |
| 217 | Me | Et | Et | Cl | CH$_2$OMe | SO$_2$Me | —CH(Me)— |
| 218 | Me | Et | i-Pr | Cl | CH$_2$OMe | SO$_2$Me | —CH(Me)— |
| 219 | Me | Et | n-Pr | Cl | CH$_2$OMe | SO$_2$Me | —CH(Me)— |
| 220 | Me | Et | n-Bu | Cl | CH$_2$OMe | SO$_2$Me | —CH(Me)— |
| 221 | Et | Et | Me | Cl | CH$_2$OMe | SO$_2$Me | —CH(Me)— |
| 222 | Et | Et | Et | Cl | CH$_2$OMe | SO$_2$Me | —CH(Me)— |
| 223 | Et | Et | i-Pr | Cl | CH$_2$OMe | SO$_2$Me | —CH(Me)— |
| 224 | Et | Et | n-Pr | Cl | CH$_2$OMe | SO$_2$Me | —CH(Me)— |
| 225 | Et | Et | n-Bu | Cl | CH$_2$OMe | SO$_2$Me | —CH(Me)— |
| 226 | i-Pr | Et | Me | Cl | CH$_2$OMe | SO$_2$Me | —CH(Me)— |
| 227 | i-Pr | Et | Et | Cl | CH$_2$OMe | SO$_2$Me | —CH(Me)— |
| 228 | i-Pr | Et | i-Pr | Cl | CH$_2$OMe | SO$_2$Me | —CH(Me)— |
| 229 | i-Pr | Et | n-Pr | Cl | CH$_2$OMe | SO$_2$Me | —CH(Me)— |
| 230 | i-Pr | Et | n-Bu | Cl | CH$_2$OMe | SO$_2$Me | —CH(Me)— |
| 231 | n-Pr | Et | Me | Cl | CH$_2$OMe | SO$_2$Me | —CH(Me)— |
| 232 | n-Pr | Et | Et | Cl | CH$_2$OMe | SO$_2$Me | —CH(Me)— |
| 233 | n-Pr | Et | i-Pr | Cl | CH$_2$OMe | SO$_2$Me | —CH(Me)— |
| 234 | n-Pr | Et | n-Pr | Cl | CH$_2$OMe | SO$_2$Me | —CH(Me)— |
| 235 | n-Pr | Et | n-Bu | Cl | CH$_2$OMe | SO$_2$Me | —CH(Me)— |
| 236 | n-Bu | Et | Me | Cl | CH$_2$OMe | SO$_2$Me | —CH(Me)— |
| 237 | n-Bu | Et | Et | Cl | CH$_2$OMe | SO$_2$Me | —CH(Me)— |
| 238 | n-Bu | Et | i-Pr | Cl | CH$_2$OMe | SO$_2$Me | —CH(Me)— |
| 239 | n-Bu | Et | n-Pr | Cl | CH$_2$OMe | SO$_2$Me | —CH(Me)— |
| 240 | n-Bu | Et | n-Bu | Cl | CH$_2$OMe | SO$_2$Me | —CH(Me)— |
| 241 | t-Bu | Et | Me | Cl | CH$_2$OMe | SO$_2$Me | —CH(Me)— |
| 242 | t-Bu | Et | Et | Cl | CH$_2$OMe | SO$_2$Me | —CH(Me)— |
| 243 | t-Bu | Et | i-Pr | Cl | CH$_2$OMe | SO$_2$Me | —CH(Me)— |
| 244 | t-Bu | Et | n-Pr | Cl | CH$_2$OMe | SO$_2$Me | —CH(Me)— |
| 245 | t-Bu | Et | n-Bu | Cl | CH$_2$OMe | SO$_2$Me | —CH(Me)— |
| 246 | Me | Et | Me | Me | C(O)OMe | SO$_2$Me | —CH(Me)— |
| 247 | Me | Et | Et | Me | C(O)OMe | SO$_2$Me | —CH(Me)— |
| 248 | Me | Et | i-Pr | Me | C(O)OMe | SO$_2$Me | —CH(Me)— |
| 249 | Me | Et | n-Pr | Me | C(O)OMe | SO$_2$Me | —CH(Me)— |
| 250 | Me | Et | n-Bu | Me | C(O)OMe | SO$_2$Me | —CH(Me)— |
| 251 | Et | Et | Me | Me | C(O)OMe | SO$_2$Me | —CH(Me)— |
| 252 | Et | Et | Et | Me | C(O)OMe | SO$_2$Me | —CH(Me)— |
| 253 | Et | Et | i-Pr | Me | C(O)OMe | SO$_2$Me | —CH(Me)— |
| 254 | Et | Et | n-Pr | Me | C(O)OMe | SO$_2$Me | —CH(Me)— |
| 255 | Et | Et | n-Bu | Me | C(O)OMe | SO$_2$Me | —CH(Me)— |
| 256 | i-Pr | Et | Me | Me | C(O)OMe | SO$_2$Me | —CH(Me)— |
| 257 | i-Pr | Et | Et | Me | C(O)OMe | SO$_2$Me | —CH(Me)— |
| 258 | i-Pr | Et | i-Pr | Me | C(O)OMe | SO$_2$Me | —CH(Me)— |
| 259 | i-Pr | Et | n-Pr | Me | C(O)OMe | SO$_2$Me | —CH(Me)— |
| 260 | i-Pr | Et | n-Bu | Me | C(O)OMe | SO$_2$Me | —CH(Me)— |
| 261 | n-Pr | Et | Me | Me | C(O)OMe | SO$_2$Me | —CH(Me)— |
| 262 | n-Pr | Et | Et | Me | C(O)OMe | SO$_2$Me | —CH(Me)— |
| 263 | n-Pr | Et | i-Pr | Me | C(O)OMe | SO$_2$Me | —CH(Me)— |
| 264 | n-Pr | Et | n-Pr | Me | C(O)OMe | SO$_2$Me | —CH(Me)— |
| 265 | n-Pr | Et | n-Bu | Me | C(O)OMe | SO$_2$Me | —CH(Me)— |
| 266 | n-Bu | Et | Me | Me | C(O)OMe | SO$_2$Me | —CH(Me)— |
| 267 | n-Bu | Et | Et | Me | C(O)OMe | SO$_2$Me | —CH(Me)— |
| 268 | n-Bu | Et | i-Pr | Me | C(O)OMe | SO$_2$Me | —CH(Me)— |
| 269 | n-Bu | Et | n-Pr | Me | C(O)OMe | SO$_2$Me | —CH(Me)— |
| 270 | n-Bu | Et | n-Bu | Me | C(O)OMe | SO$_2$Me | —CH(Me)— |
| 271 | t-Bu | Et | Me | Me | C(O)OMe | SO$_2$Me | —CH(Me)— |
| 272 | t-Bu | Et | Et | Me | C(O)OMe | SO$_2$Me | —CH(Me)— |
| 273 | t-Bu | Et | i-Pr | Me | C(O)OMe | SO$_2$Me | —CH(Me)— |
| 274 | t-Bu | Et | n-Pr | Me | C(O)OMe | SO$_2$Me | —CH(Me)— |

TABLE 1-continued (I)

| No. | R¹ | R² | R³ | R⁴ | R⁵ | R⁶ | —A— |
|---|---|---|---|---|---|---|---|
| 275 | t-Bu | Et | n-Bu | Me | C(O)OMe | SO₂Me | —CH(Me)— |
| 276 | Me | Et | Me | Cl | C(O)OMe | SO₂Me | —CH(Me)— |
| 277 | Me | Et | Et | Cl | C(O)OMe | SO₂Me | —CH(Me)— |
| 278 | Me | Et | i-Pr | Cl | C(O)OMe | SO₂Me | —CH(Me)— |
| 279 | Me | Et | n-Pr | Cl | C(O)OMe | SO₂Me | —CH(Me)— |
| 280 | Me | Et | n-Bu | Cl | C(O)OMe | SO₂Me | —CH(Me)— |
| 281 | Et | Et | Me | Cl | C(O)OMe | SO₂Me | —CH(Me)— |
| 282 | Et | Et | Et | Cl | C(O)OMe | SO₂Me | —CH(Me)— |
| 283 | Et | Et | i-Pr | Cl | C(O)OMe | SO₂Me | —CH(Me)— |
| 284 | Et | Et | n-Pr | Cl | C(O)OMe | SO₂Me | —CH(Me)— |
| 285 | Et | Et | n-Bu | Cl | C(O)OMe | SO₂Me | —CH(Me)— |
| 286 | i-Pr | Et | Me | Cl | C(O)OMe | SO₂Me | —CH(Me)— |
| 287 | i-Pr | Et | Et | Cl | C(O)OMe | SO₂Me | —CH(Me)— |
| 288 | i-Pr | Et | i-Pr | Cl | C(O)OMe | SO₂Me | —CH(Me)— |
| 289 | i-Pr | Et | n-Pr | Cl | C(O)OMe | SO₂Me | —CH(Me)— |
| 290 | i-Pr | Et | n-Bu | Cl | C(O)OMe | SO₂Me | —CH(Me)— |
| 291 | n-Pr | Et | Me | Cl | C(O)OMe | SO₂Me | —CH(Me)— |
| 292 | n-Pr | Et | Et | Cl | C(O)OMe | SO₂Me | —CH(Me)— |
| 293 | n-Pr | Et | i-Pr | Cl | C(O)OMe | SO₂Me | —CH(Me)— |
| 294 | n-Pr | Et | n-Pr | Cl | C(O)OMe | SO₂Me | —CH(Me)— |
| 295 | n-Pr | Et | n-Bu | Cl | C(O)OMe | SO₂Me | —CH(Me)— |
| 296 | n-Bu | Et | Me | Cl | C(O)OMe | SO₂Me | —CH(Me)— |
| 297 | n-Bu | Et | Et | Cl | C(O)OMe | SO₂Me | —CH(Me)— |
| 298 | n-Bu | Et | i-Pr | Cl | C(O)OMe | SO₂Me | —CH(Me)— |
| 299 | n-Bu | Et | n-Pr | Cl | C(O)OMe | SO₂Me | —CH(Me)— |
| 300 | n-Bu | Et | n-Bu | Cl | C(O)OMe | SO₂Me | —CH(Me)— |
| 301 | t-Bu | Et | Me | Cl | C(O)OMe | SO₂Me | —CH(Me)— |
| 302 | t-Bu | Et | Et | Cl | C(O)OMe | SO₂Me | —CH(Me)— |
| 303 | t-Bu | Et | i-Pr | Cl | C(O)OMe | SO₂Me | —CH(Me)— |
| 304 | t-Bu | Et | n-Pr | Cl | C(O)OMe | SO₂Me | —CH(Me)— |
| 305 | t-Bu | Et | n-Bu | Cl | C(O)OMe | SO₂Me | —CH(Me)— |
| 306 | Me | H | Et | Me | CH₂OCH(Me)₂ | SO₂Me | —CH(Me)— |
| 307 | Et | H | Et | Me | CH₂OCH(Me)₂ | SO₂Me | —CH(Me)— |
| 308 | n-Pr | H | Et | Me | CH₂OCH(Me)₂ | SO₂Me | —CH(Me)— |
| 309 | i-Pr | H | Et | Me | CH₂OCH(Me)₂ | SO₂Me | —CH(Me)— |
| 310 | Me | H | Et | Cl | CH₂OCH(Me)₂ | SO₂Me | —CH(Me)— |
| 311 | Et | H | Et | Cl | CH₂OCH(Me)₂ | SO₂Me | —CH(Me)— |
| 312 | n-Pr | H | Et | Cl | CH₂OCH(Me)₂ | SO₂Me | —CH(Me)— |
| 313 | i-Pr | H | Et | Cl | CH₂OCH(Me)₂ | SO₂Me | —CH(Me)— |

TABLE 2

| No. | ¹H-NMR δ ppm (solvent: CDCl₃, measuring instrument: JEOL-GSX (400 MHz) |
|---|---|
| 1 | 1.78 (3H, d, J = 5.6 Hz), 2.36 (3H, s), 3.10 (3H, s), 3.48 (3H, s), 3.71 (3H, s), 3.74 (3H, s), 3.82 (2H, m), 4.26 (2H, m), 6.73 (1H, m), 7.27 (1H, d, J = 8.4 Hz), 7.30 (1H, s), 7.90 (1H, d, J = 8.4 Hz). |
| 2 | 1.26 (3H, t, J = 7.1 Hz), 1.78 (3H, d, J = 5.0 Hz), 2.36 (3H, s), 3.31 (3H, s), 3.47 (3H, s), 3.71 (3H, s), 3.81 (2H, m), 4.14 (2H, q, J = 7.1 Hz), 4.25 (2H, m), 6.72 (1H, q, J = 5.0 Hz), 7.27 (1H, d, J = 8.0 Hz), 7.30 (1H, s), 7.90 (1H, d, J = 8.0 Hz). |
| 3 | 1.19 (3H, t, J = 7.0 Hz), 1.36 (3H, t, J = 7.2 Hz), 1.72 (3H, d, J = 5.2 Hz), 2.31 (3H, s), 3.25 (3H, s), 3.41 (3H, s), 3.75 (2H, m), 4.00 (2H, m), 4.06 (2H, q, J = 7.2 Hz), 6.73 (1H, q, J = 5.2 Hz), 7.20 (1H, s), 7.21 (1H, d, J = 8.2 Hz), 7.83 (1H, d, J = 8.2 Hz). |
| 4 | 1.22 (3H, d, J = 6.0 Hz), 1.26 (3H, d, J = 6.4 Hz), 1.77 (3H, d, J = 5.3 Hz), 2.36 (3H, s), 3.31 (3H, s), 3.48 (3H, s), 3.71 (3H, s), 3.82 (2H, m), 4.25 (2H, m), 4.79 (1H, m), 6.71 (1H, q, J = 5.3 Hz), 7.27 (1H, d, J = 8.4 Hz), 7.30 (1H, s), 7.90 (1H, d, J = 8.4 Hz). |
| 7 | 1.23 (3H, t, J = 7.0 Hz), 1.76 (3H, d, J = 5.2 Hz), 2.41 (3H, s), 3.20 (3H, s), 3.48 (3H, s), 4.11 (2H, q, J = 7.0 Hz), 4.94 (2H, s), 6.72 (1H, q, J = 5.2 Hz), 7.23 (1H, s), 7.42 (1H, d, J = 7.6 Hz), 8.03 (1H, d, J = 7.6 Hz). |
| 11 | 1.25 (3H, t, J = 6.8 Hz), 1.45 (3H, d, J = 5.6 Hz), 1.97 (3H, s), 2.35 (3H, s), 3.30 (3H, s), 3.48 (3H, s), 3.65 (3H, s), 3.82 (3H, t, J = 4.4 Hz), 4.13 (2H, q, J = 6.8 Hz), 4.25 (2H, t, J = 4.4 Hz), 6.23 (1H, q, J = 5.6 Hz), 7.23 (1H, d, J = 8.4 Hz), 7.91 (1H, d, J = 8.4 Hz) |
| 15 | 1.19 (3H, t, J = 6.8 Hz), 1.71 (3H, d, J = 5.6 Hz), 2.38 (3H, s), 3.12 (3H, s), 3.64 (3H, s), 3.96 (2H, q, J = 8.0 Hz), 4.06 (2H, q, J = 6.8 Hz), 5.17 (2H, s), 6.68 (1H, q, J = 5.6 Hz), 7.21 (1H, s), 7.42 (1H, d, J = 8.0 Hz), 8.00 (1H, d, J = 8.0 Hz) |
| 18 | 1.24 (3H, t, J = 7.0 Hz), 1.42 (6H, m), 1.77 (3H, d, J = 5.6 Hz), 2.35 (3H, s), 3.30 (3H, s), 3.46 (3H, s), 3.80 (2H, m), 4.10 (2H, q, J = 7.0 Hz), 4.23 (2H, m), 4.66 (1H, m), 6.76 (1H, q, J = 5.6 Hz), 7.25 (1H, s), 7.28 (1H, d, J = 8.0 Hz), 7.87 (1H, d, J = 8.0 Hz). |
| 19 | 0.86 (3H, t, J = 7.2 Hz), 1.58 (2H, m), 1.71 (3H, d, J = 5.2 Hz), 2.30 (3H, s), 3.25 (3H, s), 3.42 (3H, s), 3.65 (3H, s), 3.76 (2H, m), 3.97 (2H, t, J = 6.8 Hz), 4.19 (2H, m), 6.67 (1H, q, J = 5.2 Hz), 7.20 (1H, s), 7.22 (1H, d, J = 7.6 Hz), 7.84 (1H, d, J = 7.6 Hz). |
| 20 | 0.89 (3H, t, J = 7.2 Hz), 1.32 (2H, m), 1.57 (2H, m), 1.75 (3H, d, J = 5.2 Hz), 2.34 (3H, s), 3.29 (3H, s), 3.45 (3H, s), 3.68 (3H, s), 3.79 (2H, m), 4.05 (2H, t, J = 6.4 Hz), 4.23 (2H, m), 6.70 (1H, q, J = 5.2 Hz), 7.25 (1H, d, J = 8.0 Hz), 7.27 (1H, s), 7.87 (1H, d, J = 8.0 Hz). |
| 21 | 1.24 (3H, t, J = 7.6 Hz), 1.76 (3H, d, J = 5.2 Hz), 2.32 (3H, s), 3.12 (3H, s), 3.69 (3H, s), 3.98 (3H, s), 4.11 (2H, q, J = 7.6 Hz), 6.72 (1H, m), 7.27 (1H, s), 7.52 (1H, d, J = 8.0 Hz), 7.94 (1H, d, J = 8.0 Hz). |

Now, Test Examples will be described.

Test Example 1

Upland field soil was put into a 1/170,000 hectare pot, and seeds of various plants were sown. When the respective plants reached predetermined leaf stage ((1) barnyardgrass (*Echinochloa crus-galli* L.): 1.0 to 3.3 leaf stage, (2) crabgrass (*Digitaria sanguinalis* L.): 1.2 to 3.0 leaf stage, (3) green foxtail (*Setaria viridis* L.): 1.5 to 3.3 leaf stage, (4) redroot pigweed (*Amaranthus retroflexus* L.): 0.1 to 2.0 leaf stage, (5) prickly sida (*Sida spinosa* L.): cotyledon stage to 2.0 leaf stage, (6) velvetleaf (*Abutilon theophrasti* MEDIC.): 0.1 to 2.0 leaf stage, (7) rice (*Oryza sativa* L.): 1.3 to 3.0 leaf stage, (8) corn (*Zea mays* L.): 2.5 to 3.4 leaf stage, and (9) soybean (*Glycine max* Merr.): primary leaf stage to 0.3 leaf stage), wettable powders or emulsifiable concentrates of the compounds of the present invention prepared in accordance with a conventional preparation method, were weighed so that the active ingredients became the prescribed amounts, and diluted with water in an amount corresponding to 500 liter per 1 hectare (containing 0.1 vol % of an agricultural spreader ("KUSARINOH", manufactured by NIHON NOHYAKU CO., LTD.)). The spray solutions thus prepared were applied for foliar treatment by a small sprayer.

On the 21st day after application, the state of growth of the respective plants was visually observed, and the herbicidal effect was evaluated by a growth inhibition rate (%) of 0 (equivalent to the non-treated area) to 100% (complete kill). The results are shown in Table 3.

TABLE 3

| Compound No. | Amount of active ingredient (g/ha) | Growth inhibition rate (%) | | | | | | | | | Date of observation |
|---|---|---|---|---|---|---|---|---|---|---|---|
| | | Barnyardgrass | Crabgrass | Green foxtail | Redroot pigweed | Prickly sida | Velvetleaf | Rice | Corn | Soybean | |
| 1 | 7 | 100 | 90 | 100 | 100 | 60 | 100 | 80 | 0 | 95 | 21 |
| 2 | 7 | 100 | 95 | 95 | 100 | 40 | 95 | 80 | 0 | 80 | 21 |
|   | 63 | 100 | 100 | 100 | 100 | 85 | 100 | 70 | 0 | 98 | 21 |
| 3 | 7 | 95 | 95 | 100 | 90 | 10 | 90 | 80 | 0 | 70 | 21 |
| 4 | 7 | 100 | 90 | 100 | 90 | 40 | 98 | 30 | 0 | 90 | 21 |
| 7 | 7 | 95 | 90 | 90 | 85 | 80 | 98 | 70 | 0 | 95 | 21 |
| 11 | 7 | 90 | 90 | 90 | 80 | 10 | 60 | 80 | 0 | 70 | 21 |
| 15 | 7 | 70 | 95 | 75 | 90 | 0 | 98 | 40 | 10 | 75 | 21 |
| 18 | 7 | 95 | 95 | 90 | 95 | 30 | 95 | 70 | 0 | 80 | 21 |
| 19 | 7 | 95 | 90 | 100 | 95 | 30 | 95 | 80 | 0 | 80 | 21 |
| 20 | 7 | 100 | 100 | 100 | 100 | 40 | 100 | 50 | 0 | 80 | 21 |
| 21 | 7 | 90 | 90 | 80 | 90 | — | 85 | 80 | 0 | 95 | 21 |

Test Example 2

Upland field soil was put into a 1/170,000 hectare pot, and seeds of various plants (barnyardgrass (*Echinochloa crusgalli* L.), crabgrass (*Digitaria sanguinalis* L.), green foxtail (*Setaria viridis* L.), redroot pigweed (*Amaranthus retroflexus* L.), prickly sida (*Sida spinosa* L.), velvetleaf (*Abutilon theophrasti* MEDIC.), rice (*oryza sativa* L.), corn (*Zea mays* L.) and soybean (*Glycine max* Merr.)) were sown. On the day after sowing, wettable powders or emulsifiable concentrates of the compounds of the present invention prepared in accordance with a conventional preparation method, were weighed so that the active ingredients became the prescribed amounts, and diluted with water in an amount corresponding to 500 liter per 1 hectare, followed by soil application with a small sprayer.

On the 19th to 22nd day after the application, the state of growth of the respective plants was visually observed, and the herbicidal effect was evaluated by a growth inhibition rate (%) of from 0 (equivalent to the non-treated area) to 1000 (complete kill). The results are shown in Table 4.

Test Example 3

Upland field soil was put into a 1/1,000,000 hectare pot, and seeds of various plants were sown. When the respective plants reached predetermined leaf stage ((1) velvetleaf (*Abutilon theophrasti* MEDIC.): 3.3 to 4.3 leaf stage, (2) guineagrass (Panicum maximum Jacq.): 3.5 to 4.3 leaf stage, (3) green foxtail (*Setaria viridis* L.): 4.0 to 4.5 leaf stage, and (4) corn (*Zea mays* L.): 4.0 to 4.3 leaf stage, a wettable powder of compound No. 2 of the present invention, an emulsifiable concentrate of the following Reference Compound 1 and a wettable powder of the following Reference Compound 2, prepared in accordance with a conventional preparation method, were weighed so that the active ingredients became the prescribed amounts, and diluted with water in an amount corresponding to 300 liter per 1 hectare (containing 0.5 vol % of an agricultural spreader (MSO concentrate, manufactured by Cognis Corporation). The spray solutions thus prepared were applied for foliar treatment by a small sprayer.

TABLE 4

| Compound No. | Amount of active ingredient (g/ha) | Growth inhibition rate (%) | | | | | | | | | Date of observation |
|---|---|---|---|---|---|---|---|---|---|---|---|
| | | Barnyardgrass | Crabgrass | Green foxtail | Redroot pigweed | Prickly sida | Velvetleaf | Rice | Corn | Soybean | |
| 1 | 250 | 100 | 100 | 90 | 100 | 90 | 100 | 100 | 0 | 0 | 19 |
| 2 | 250 | 100 | 100 | 100 | 100 | 70 | 60 | 98 | 0 | 0 | 21 |
| 3 | 250 | 100 | 100 | 100 | 100 | 50 | 80 | 100 | 0 | 20 | 19 |
| 4 | 250 | 100 | 100 | 95 | 95 | 90 | 70 | 90 | 0 | 0 | 20 |
| 7 | 250 | 100 | 90 | 40 | 80 | 80 | 70 | 90 | 0 | 0 | 21 |
| 11 | 250 | 100 | 100 | 100 | 100 | 40 | 70 | 100 | 0 | 20 | 19 |
| 15 | 250 | 100 | 100 | 100 | 100 | 70 | 100 | 100 | 0 | 0 | 19 |
| 18 | 250 | 100 | 100 | 100 | 100 | 70 | 100 | 100 | 0 | — | 22 |
| 19 | 250 | 100 | 100 | 100 | 100 | 60 | 98 | 100 | 0 | 40 | 19 |
| 20 | 250 | 100 | 100 | 100 | 100 | 70 | 100 | 100 | 0 | 30 | 19 |
| 21 | 250 | 100 | 100 | 100 | 100 | 60 | 90 | 100 | 0 | 50 | 19 |

On the 17th to 22nd day after application, the state of growth of the respective plants was visually observed, and the herbicidal effect was evaluated by a growth inhibition rate (%) of 0 (equivalent to the non-treated area) to 100% (complete kill). The results are shown in Tables 5 to 8.

TABLE 5

| Compound No. | Amount of active ingredient (g/ha) | Growth inhibition rate (%) (22nd day after application) Velvet leaf |
|---|---|---|
| 2 | 15 | 94 |
| Reference Compound 1 | 15 | 20 |
| Reference Compound 2 | 15 | 40 |

TABLE 6

| Compound No. | Amount of active ingredient (g/ha) | Growth inhibition rate (%) (18th day after application) Guineagrass |
|---|---|---|
| 2 | 3.5 | 90 |
| Reference Compound 1 | 3.5 | 0 |
| Reference Compound 2 | 3.5 | 0 |

TABLE 7

| Compound No. | Amount of active ingredient (g/ha) | Growth inhibition rate (%) (17th day after application) Green foxtail |
|---|---|---|
| 2 | 3.5 | 93 |
|   | 7 | 98 |
| Reference Compound 1 | 3.5 | 35 |
|   | 7 | 55 |
| Reference Compound 2 | 3.5 | 30 |
|   | 7 | 45 |

TABLE 8

| Compound No. | Amount of active ingredient (g/ha) | Growth inhibition rate (%) (21st day after application) Corn |
|---|---|---|
| 2 | 120 | 4 |
| Reference Compound 2 | 120 | 28 |

Reference Compound 1:

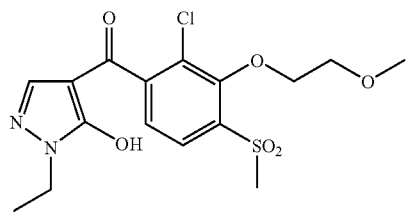

(Compound No. 1 disclosed at page 18 of EP0352543A1)

Reference Compound 2:

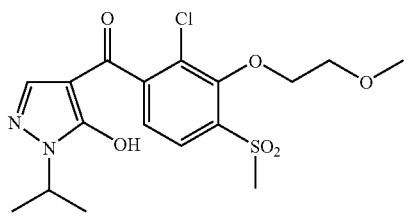

(Compound No. 20 disclosed at page 21 of EP0352543A1)

Test Example 4

Paddy field soil was put into a 1/1,000,000 hectare pot, and seeds of barnyardgrass (*Echinochloa oryzicola* vasing.) and Japanese bulrush (*Scirpus juncoides*) were sown and lightly covered with soil. Then, pot was left to stand in a greenhouse in a state irrigated to a water depth of from 0.5 to 1 cm, and next day or two days later, tubers of Japanese ribbon waparo (*Sagittaria pygmaea*) were planted. Then, the irrigated water depth was maintained to be from 3 to 4 cm, and when barnyardgrass and Japanese bulrush reached 0.5 leaf stage, and Japanese ribbon waparo reached primary leaf stage, a water diluted solution of a wettable powder or an emulsifieable concentrate of the compound of the present invention prepared in accordance with a conventional preparation method, was uniformly dropwise applied by a pipette so that the amount of active ingredients would be a prescribed amount. Further, paddy field soil was put into a 1/1,000,000 pot, followed by soil puddling to an irrigated water depth of from 3 to 4 cm. Next day, rice (*Oryza sativa* L.) (var.: Nihonbare) of two leaf stage was transplanted in a transplantation depth of 3 cm. On the 4th day after transplantation, the compound of the present invention was applied in the same manner as described above.

On the 14th day after application, the state of growth of barnyardgrass, Japanese bulrush and Japanese ribbon waparo was visually observed, and on the 21st day after application, the state of growth of rice was visually observed, and the herbicidal effect was evaluated by a growth inhibition rate (%) of 0 (equivalent to the non-treated area) to 100% (complete kill). The results are shown in Table 9.

TABLE 9

| Compound No. | Amount of active ingredient (g/ha) | Growth inhibition rate (%) | | | |
|---|---|---|---|---|---|
| | | barnyardgrass | Japanese bulrush | Japanese ribbon waparo | Rice |
| 1 | 63 | 100 | 70 | 98 | 30 |
| 2 | 63 | 100 | 60 | 95 | 50 |
| 3 | 63 | 100 | 95 | 90 | 40 |
| 4 | 63 | 100 | 95 | 90 | 50 |
| 7 | 63 | 100 | 70 | 60 | 70 |
| 11 | 63 | 98 | 100 | 60 | 60 |
| 15 | 63 | 100 | 60 | — | 10 |
| 18 | 63 | 100 | 90 | 90 | 0 |
| 19 | 63 | 100 | 95 | 95 | 20 |
| 20 | 63 | 100 | 80 | — | 50 |
| 21 | 63 | 100 | 70 | 70 | 10 |

Now, Formulation Examples of the present invention will be described.

Formulation Example 1

| | |
|---|---|
| (1) The compound of the present invention | 75 parts by weight |
| (2) Geropon T-77 (tradename, manufactured by Rhone-Poulenc) | 14.5 parts by weight |
| 3) NaCl | 10 parts by weight |
| 4) Dextrin | 0.5 part by weight |

The above components are placed in a high-speed mixing granulator, admixed with 20 wt % of water, granulated, and dried to obtain water-dispersible granules.

Formulation Example 2

| | |
|---|---|
| (1) Kaolin | 78 parts by weight |
| (2) Laveline FAN (tradename, manufactured by DAI-ICHI KOGYO SEIYAKU CO., LTD.) | 2 parts by weight |
| (3) Sorpol 5039 (tradename, manufactured by TOHO Chemical Industry Co., Ltd.) | 5 parts by weight |
| (4) Carplex (tradename, manufactured by DSL. Japan Co., Ltd.) | 15 parts by weight |

The mixture of the above components (1) to (4) and the compound of the present invention are mixed in a weight ratio of 9:1 to obtain a wettable powder.

Formulation Example 3

| | |
|---|---|
| (1) Hi-Filler No. 10 (tradename, manufactured by Matsumura Sangyo Co., Ltd.) | 33 parts by weight |
| (2) Sorpol 5050 (tradename, manufactured by TOHO Chemical Industry Co., Ltd.) | 3 parts by weight |
| (3) Sorpol 5073 (tradename, manufactured by TOHO Chemical Industry Co., Ltd.) | 4 parts by weight |
| (4) The compound of the present invention | 60 parts by weight |

The above compounds (1) to (4) are mixed to obtain a wettable powder.

Formulation Example 4

| | |
|---|---|
| (1) The compound of the present invention | 4 parts by weight |
| (2) Bentonite | 30 parts by weight |
| (3) Calcium carbonate | 61.5 parts by weight |
| (4) Toxanon GR-31A (tradename, manufactured by Sanyo Chemical Industries Co., Ltd.) | 3 parts by weight |
| (5) Calcium lignin sulfonate | 1.5 parts by weight |

Pulverized component (1) and components (2) and (3) are preliminarily mixed, and then components (4) and (5) and water are mixed thereto. The mixture is extruded and granulated, followed by drying and sieving to obtain granules.

Formulation Example 5

| | |
|---|---|
| (1) The compound of the present invention | 30 parts by weight |
| (2) Zieclite (tradename, manufactured by Zieclite Co., Ltd.) | 60 parts by weight |
| (3) New Kalgen WG-1 (tradename, manufactured by TAKEMOTO OIL & FAT CO., LTD.) | 5 parts by weight |
| (4) New Kalgen FS-7 (tradename, manufactured by TAKEMOTO OIL & FAT CO., LTD.) | 5 parts by weight |

Components (1), (2) and (3) are mixed and passed through a pulverizer, and then component (4) is added thereto. The mixture is kneaded and then extruded and granulated, followed by drying and sieving to obtain water dispersible granules.

Formulation Example 6

| | |
|---|---|
| (1) The compound of the present invention | 28 parts by weight |
| (2) Soprophor FL (tradename, manufactured by Rhone-Poulenc) | 2 parts by weight |
| (3) Sorpol 335 (tradename, manufactured by TOHO Chemical Industry Co., Ltd.) | 1 part by weight |
| (4) IP solvent 1620 (tradename, manufactured by Idemitsu Petrochemical Co., Ltd.) | 32 parts by weight |
| (5) Ethylene glycol | 6 parts by weight |
| (6) Water | 31 parts by weight |

The above components (1) to (6) are mixed and pulverized by a wet-grinding machine (Dyno-mill) to obtain a water-based suspension concentrate.

The invention claimed is:

1. A benzoylpyrazole compound represented by the formula (I) or its salt:

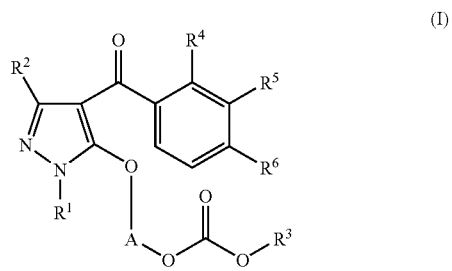

(I)

wherein $R^1$ is alkyl, $R^2$ is a hydrogen atom or alkyl, $R^3$ is alkyl, $R^4$ is alkyl or halogen, $R^5$ is alkyl substituted by one $Y^1$, haloalkoxy, alkoxy substituted by one $Y^2$, or alkoxycarbonyl, $R^6$ is alkylsulfonyl, A is alkylene substituted by at least one alkyl, $Y^1$ is alkoxy or haloalkoxy, and $Y^2$ is alkoxy.

2. The benzoylpyrazole compound or its salt according to claim 1, wherein $R^1$ is alkyl, $R^2$ is a hydrogen atom or alkyl, $R^3$ is alkyl, $R^4$ is alkyl, $R^5$ is alkyl substituted by one $Y^1$, alkoxy substituted by one $Y^2$, or alkoxycarbonyl, $R^6$ is alkylsulfonyl, A is alkylene substituted by one alkyl, $Y^1$ is alkoxy or haloalkoxy, and $Y^2$ is alkoxy.

3. The benzoylpyrazole compound or its salt according to claim 2, wherein $R^2$ is a hydrogen atom, and $R^5$ is alkoxy substituted by one alkoxy.

4. The benzoylpyrazole compound or its salt according to claim 2, wherein $R^1$ is methyl, $R^2$ is a hydrogen atom, $R^3$ is methyl, $R^4$ is methyl, $R^5$ is 2-methoxyethoxy, $R^6$ is methylsulfonyl, and A is represented by the formula (a-1):

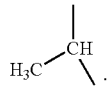
(a-1)

5. The benzoylpyrazole compound or its salt according to claim 2, wherein $R^1$ is methyl, $R^2$ is a hydrogen atom, $R^3$ is ethyl, $R^4$ is methyl, $R^5$ is 2-methoxyethoxy, $R^6$ is methylsulfonyl, and A is represented by the formula (a-1):

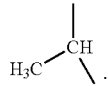
(a-1)

6. The benzoylpyrazole compound or its salt according to claim 2, wherein $R^1$ is methyl, $R^2$ is a hydrogen atom, $R^3$ is isopropyl, $R^4$ is methyl, $R^5$ is 2-methoxyethoxy, $R^6$ is methylsulfonyl, and A is represented by the formula

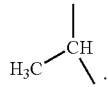
(a-1)

7. The benzoylpyrazole compound or its salt according to claim 2, wherein $R^1$ is methyl, $R^2$ is a hydrogen atom, $R^3$ is ethyl, $R^4$ is methyl, $R^5$ is methoxymethyl, $R^6$ is methylsulfonyl, and A is represented by the formula (a-1):

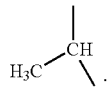
(a-1)

8. A process for producing a benzoylpyrazole compound represented by the formula (I) or its salt:

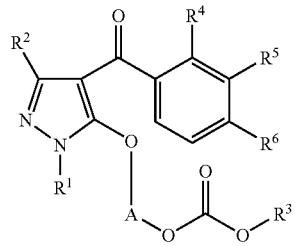
(I)

wherein $R^1$ is alkyl, $R^2$ is a hydrogen atom or alkyl, $R^3$ is alkyl, $R^4$ is alkyl or halogen, $R^5$ is alkyl substituted by one $Y^1$, haloalkoxy, alkoxy substituted by one $Y^2$, or alkoxycarbonyl, $R^6$ is alkylsulfonyl, A is alkylene substituted by at least one alkyl, $Y^1$ is alkoxy or haloalkoxy, and $Y^2$ is alkoxy, which comprises reacting a compound represented by the formula (II):

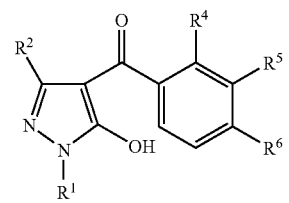
(II)

wherein $R^1$, $R^2$, $R^4$, $R^5$ and $R^6$ are as defined above, with a compound represented by the formula (III):

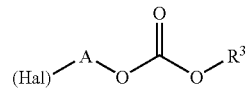
(III)

wherein Hal is halogen, and $R^3$ and A are as defined above.

9. A herbicide containing the benzoylpyrazole compound or its salt as defined in claim 1 as an active ingredient.

10. A method for controlling undesired plants or inhibiting their growth, which comprises applying a herbicidally effective amount of the benzoylpyrazole compound or its salt as defined in claim 1 to the undesired plants or to a place where they grow.

* * * * *